(12) United States Patent
Margel et al.

(10) Patent No.: US 10,508,126 B2
(45) Date of Patent: Dec. 17, 2019

(54) BISPHOSPHONATES VINYLIC MONOMERS AND POLYMERS AND USES THEREOF

(71) Applicant: BAR-ILAN UNIVERSITY, Ramat Gan (IL)

(72) Inventors: Shlomo Margel, Rehovot (IL); Dana Mizrahi, Rishon Lezion (IL); Eran Gluz, Hod Hasharon (IL); Ravit Chen, Givataim (IL)

(73) Assignee: Bar-Ilan University, Ramat Gan (IL)

( * ) Notice: Subject to any disclaimer, the term of this patent is extended or adjusted under 35 U.S.C. 154(b) by 0 days.

(21) Appl. No.: 15/888,496

(22) Filed: Feb. 5, 2018

(65) Prior Publication Data

US 2018/0155374 A1 Jun. 7, 2018

Related U.S. Application Data

(63) Continuation of application No. 14/401,964, filed as application No. PCT/IB2013/054135 on May 20, 2013, now Pat. No. 9,884,880.

(Continued)

(51) Int. Cl.
*A61K 9/00* (2006.01)
*C07F 9/38* (2006.01)
(Continued)

(52) U.S. Cl.
CPC .......... *C07F 9/3873* (2013.01); *A61K 9/1635* (2013.01); *A61K 31/663* (2013.01);
(Continued)

(58) Field of Classification Search
CPC .................................................... C07F 9/3873
See application file for complete search history.

(56) References Cited

U.S. PATENT DOCUMENTS

| 4,440,646 A | 4/1984 | Budnick |
| 2008/0153784 A1 | 6/2008 | Zhang et al. |
| 2009/0227544 A1 | 9/2009 | Karpeisky et al. |

FOREIGN PATENT DOCUMENTS

| WO | 2004/060327 A1 | 7/2004 |
| WO | 2006102117 | 9/2006 |
| WO | 2011062965 | 5/2011 |

OTHER PUBLICATIONS

Elan Gluz, Dana M Mizrahi, Shlomo Margel, Synthesis and characterization of new poly (ethylene glycol) pisphosphonate vinylic monomer and non-fluorescent and NIR-fluorescent bisphosphonate micrometer-sized particles, Polymer 54, 2013, pp. 565-571.

(Continued)

*Primary Examiner* — Paul W Dickinson
(74) *Attorney, Agent, or Firm* — Roach Brown McCarthy & Bruber, P.C.; Kevin D. McCarthy

(57) ABSTRACT

A compound or a polymer is claimed. A first formula can be

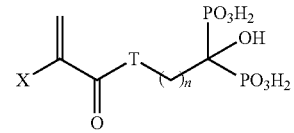

wherein X is H, CH$_3$, CN, phenyl, substituted phenyl, (CH$_2$)$_m$Z, or phenyl(CH$_2$)$_m$Z; T is O, N, S or NH; m equals 1 to 20; n equals 1-100; and Z is CN, NH$_2$, Thiol, OH, or CO$_2$H. The second formula is:

(Continued)

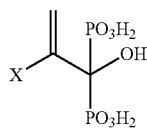

wherein X is H, CH₃, CN, phenyl, substituted phenyl, $(CH_2)_m Z$, or phenyl$(CH_2)_m Z$; and Z is CN, NH₂, Thiol, OH, or CO₂H. The third formula is

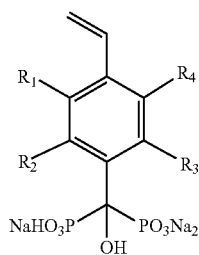

wherein: $R_1$, $R_2$, $R_3$, and $R_4$ are independently: H, CH₃, OH, or a halogen.

14 Claims, 15 Drawing Sheets

Related U.S. Application Data

(60) Provisional application No. 61/649,306, filed on May 20, 2012.

(51) Int. Cl.
- C07F 9/6558 (2006.01)
- A61K 49/00 (2006.01)
- A61K 47/69 (2017.01)
- A61K 9/16 (2006.01)
- A61K 31/663 (2006.01)
- A61K 31/80 (2006.01)
- A61K 45/06 (2006.01)
- C08F 220/60 (2006.01)

(52) U.S. Cl.
CPC .............. *A61K 31/80* (2013.01); *A61K 45/06* (2013.01); *A61K 47/6933* (2017.08); *A61K 49/0034* (2013.01); *A61K 49/0052* (2013.01); *A61K 49/0054* (2013.01); *A61K 49/0093* (2013.01); *C07F 9/386* (2013.01); *C07F 9/3882* (2013.01); *C07F 9/65583* (2013.01); *C08F 220/60* (2013.01); *A61K 2123/00* (2013.01)

(56) References Cited

OTHER PUBLICATIONS

Ravit Chen, Jenny Goldshtein, Shlomo Margel, Synthesis and Characterization of Hydroxy-Bisphosphonate Micrometer-Sized Particles by Dispersion Polymerization of a New Styrylbisphosphonate Monomer, Polymer Chemistry, Feb. 19, 2013, pp. 2199-2207.

Yang et al., "Direct "click" Synthesis of Hybrid Bisphosphonate—Hyaluronic Acid Hydrogel in Aqueous Solution for Biomineralization", Chemistry of Materials, vol. 24, No. 9, pp. 1690-1697, Apr. 2012, 8 pages.

Wang et al., "The first pamidronate containing polymer and copolymer", Chemical Communications, No. 26, 2006, pp. 2795-2797. 3 pages.

Communication and Supplementary European Search Report for a a counterpart foreign application—European Application No. 13794482.3; dated Apr. 5, 2016 18 pages.

BISPHOSPHONATES VINYLIC MONOMERS AND POLYMERS AND USES THEREOF

FIELD OF INVENTION

The present invention provides novel bisphosphonates vinylic monomers, polymers, and particles that have utility as biologically active molecule (such as drugs) carriers, coatings and for imaging/radiology applications.

BACKGROUND OF THE INVENTION

Bisphosphonates (BPs, FIG. 1) are non-hydrolyzable pyrophosphate analogs with high affinity to hydroxyapatite due to their ability to create bidentate or tridentate chelates with calcium ions. Consequently, Bisphosphonates leads to strong interactions with dentin, enamel and bones. Up to date, the wide clinical use of approved Bisphosphonates is for treatment of bone diseases associated with bone fragmentation, such as bone malignancies, osteoporosis, Paget's disease, etc. In addition to their strong affinity to calcium in the bone mineral, Bisphosphonates (especially those bearing OH) accelerate osteoblasts action, while strongly inhibiting osteoclasts, thus contributing to enhanced bone formation.

It was recently found that certain Bisphosphonates induced reduction in bone resorption, inhibited tumor growth and metastases formation, but had little effect on metastases already present in the bone. Hence, it is important to give prophylactic Bisphosphonates whenever skeletal metastases formation is a possible outcome of the cancer.

Numerous attempts to deliver drugs to the bones, via direct conjugation to Bisphosphonates, have been accomplished. A recent work reported a typical conjugation of Bisphosphonates to drugs via an anhydride with a phosphate bridge (Karpeisky, A., Zinnen, S. Bone targeted therapeutics and methods of making and using the same. US Pat Appl. 2009/0227544). However, the utilization of Bisphosphonates as bone-seeking agents has been much more successful in the field of bone-imaging. Complexes of Bisphosphonates with Tc and Re are widely used for the imaging of bone metastases using single photon emission computed tomography (SPECT) or planar scintigraphy. Recent studies attempted to use direct conjugates of Bisphosphonates with far-red and near IR fluorescent dyes, for non-isotopic imaging of bone turnover (McKenna, C. E., Sun, S., Blazewska, K. M., Kashemirov, B. A., Roelofs, A. J., Coxon, F. P., Rogers, M. J., Ebetino, F. H. Synthesis of novel risedronate and related conjugates with Rhodamine Red-X and Alexa Fluor 647: New fluorescent probes for bone active drugs. Abstracts of Papers, 238th ACS National Meeting, Washington, D.C., United States, August 2009.).

Due to their highly hydrophilic properties, Bisphosphonates exhibit low skeletal bioavailability (around 1%). Over the years, most of the studies in this field were focused at increasing the Bisphosphonates uptake. Bisphosphonates have been conjugated to proteins, peptides and biocompatible polymers or encapsulated in various polymeric formulations, to allow better absorbing and slow-release of these drugs (Karavas, E., Koutris, E., Politis, S., Samara, V., Bikiaris, D. Pharmaceutical compositions containing bisphosphonates. WO 2009/018834). Some non-hydroxy Bisphosphonate conjugations to nanoparticles have also been investigated, but in most cases where Bisphosphonate-polymer conjugates were prepared, the Bisphosphonate was coupled to an existing polymer, usually via a spacer arm.

Bones and teeth are microstructurally and compositionally complex containing both organic and inorganic constituents. Common to these hard tissues are hydroxyapatite and collagen. The biocompatibility of synthetic hydroxyapatite is well documented, making it an attractive candidate as a biomaterial. Since hard tissues are composites they exhibit physical properties, which cannot be realized solely by a mineral constituent.

Thus, generation of such hard tissues with desired physical properties requires combination of the mineral with polymeric component. Greish and Brown described the formation of biocompatible organic-inorganic composites by reaction between tetracalcium phosphate and poly(vinyl phosphonic acid) (Greish, Y. E.; Brown, P. W. Chemically formed HAp-Ca poly(vinyl phosphonate) composites. Biomaterials 2001, 22, 807-816).

Schöller et al described the formation of hybrid particles via mineralization of calcium phosphate on the surface of copolymer particles composed of poly(vinylphosphonic acid) or poly(vinylbenzylphosphonic acid) and polystyrene (Schöller, K.; Ethirajan, A.; Zeller, A. Landfester, K. Biomimetic rout to calcium phosphate coated polymeric nanoparticles: Influence of different functional groups and pH. Macromolecular Chemistry and Physics 2011, 212, 1165-1175).

Mou et al described, for the first time, the synthesis and use of phosphorous-containing monomer for dental applications (Mou, L.; Singh, G.; Nicholson, J. W. Synthesis of a hydrophilic phosphonic acid monomer fordental materials. Chemical communication 2000, 345-346). They reported that the incorporation of a phosphonic function into monomer structures results in an increase biocompatibility and adhesion to the tooth, due to chelation with calcium ions in the tooth surface. Later on, diverse acrylic monomers containing phosphoric or phosphonic acids were prepared and evaluated as self-etching adhesive system for bonding of resin composite to enamel or dentin.

Alendronate, a commercial Bisphosphonate compound containing terminal primary amino group, was bound to various compounds and particles by the interaction of the primary amine group with appropriate functional groups. For example, Rayment et al. described the formation of methacrylate alendronate monomer (MA-AL. FIG. 2) and the polymerization of the MA-AL monomer by gamma radiation for wound healing. The MA-AL monomer was formed by interaction of methacryloyl chloride with alendronate (US patent application 2010/0172860). Katsumi et al described the formation of PEG-conjugated alendronate by binding alendronate to Methyl-PEO$_8$-NHS (Katsumi. H, Takashima. M, Sano. J, Nishiyama. K, kitamura. N, Sakane. T, Hibi. T, Yamamoto. A., Development of Polyethylene Glycol-Conjugated Alendronate, a Novel Nitrogen-Containing Bisphosphonates Derivative: Evaluation of Absorption, Safety, and Effect After Intrapulmonary Administration in Rats. J. of Pharmaceutical Sciences 100 (9), 3783 (2011)). Benyettou et al. coated iron oxide nanoparticles with alendronate by physical adsorption of the alendronate to the surface of non-coated iron oxide particles (Benyettou. F, Chebbi. I, Motte. L, Sekskek. O., Magnetoliposome for alendronate delivery, J. of Mater. Chem., 21, 4813, 2011).

SUMMARY OF THE INVENTION

In one embodiment, this invention provides a compound comprising formula I:

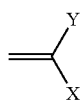

wherein
X is H, CH$_3$, CN, Phenyl or a substituted Phenyl, or (CH$_2$)$_m$Z, phenyl(CH$_2$)$_m$Z;
Y is bisphosphonate, hydroxyl-bisphosphonate, phenyl-bisphosphonate, phenyl-hydroxyl bisphosphonate, substituted phenyl-bisphosphonate, phenyl (CH$_2$)$_n$ bisphosphonate, or substituted phenyl(CH$_2$)$_n$BP, (polyethylene glycol)$_n$-bisphosphonate, (polyethyleneimine)$_n$-bisphosphonate;
Z is CN, NH$_2$, Thiol, OH, or CO$_2$H;
m equals 1 to 20; and
n equals 1 to 200.

In another embodiment, this invention further provides a compound comprising formula II:

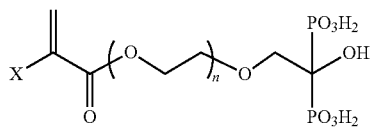

Wherein
X is H, CH$_3$, CN, Phenyl or a substituted Phenyl, (CH$_2$)$_m$Z, or phenyl(CH$_2$)$_m$Z;
Z is CN, NH$_2$, Thiol, OH, or CO$_2$H;
m equals 1 to 20; and
n equals 1 to 200.

In another embodiment, this invention further provides a compound comprising formula III:

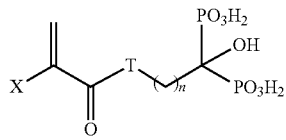

Wherein
X is H, CH$_3$, CN, Phenyl or a substituted Phenyl, (CH$_2$)$_m$Z, or phenyl(CH$_2$)$_m$Z;
T is O, N, S or NH;
Z is CN, NH$_2$, Thiol, OH, or CO$_2$H;
m equals 1 to 20; and
n equals 1 to 200.

In another embodiment, this invention further provides a compound comprising formula IV:

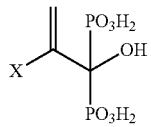

Wherein
X is H, CH$_3$, OH, Phenyl, substituted Phenyl, (CH$_2$)$_m$Z, or phenyl(CH$_2$)$_m$Z;
Z functional group, such as: CN, NH$_2$, Thiol, OH, or CO$_2$H; and m equals 1 to 20

In another embodiment, this invention further provides a compound comprising formula V:

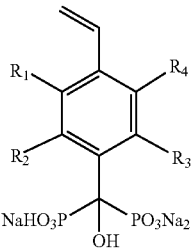

Wherein
R$_1$, R$_2$, R$_3$, and R$_4$ are independently: H, CH$_3$, OH, or a halogen, In another embodiment, this invention further provides a polymer or a particle comprising any of the above monomers or any combination of the above monomers. In another embodiment, the particle or polymer further comprises a biologically active molecule.

In another embodiment, this invention further provides a method of making a particle, comprising the step of free radical homopolymerization or copolymerization of monomers of the any of the above compounds in the presence of: (a) a free radical homopolymerization or copolymerization initiator; (b) a free radical homopolymerization or copolymerization stabilizer.

In another embodiment, this invention further provides a method of imaging a bone in a subject, comprising the step of administering to the subject a composition comprising an effective amount of a particle comprising a dye; and irradiating the dye.

In another embodiment, this invention further provides a method of delivering a biologically active compound to a bone or a tooth in a subject, comprising the step of administering to the subject a composition comprising an effective amount of a particle wherein the particle comprises a bone or a tooth bioactive agent.

In another embodiment, this invention further provides a method of treating a bone or a tooth related disease in a subject, comprising the step of administering to the subject a composition comprising an effective amount of a particle comprising a bone or a tooth related disease drug.

DETAILED DESCRIPTION OF THE INVENTION

Figure 1:
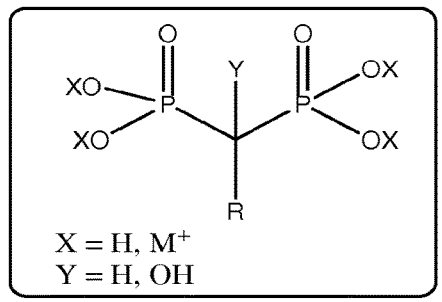
FIG. 1. A General structure of BPs.
Figure 2:
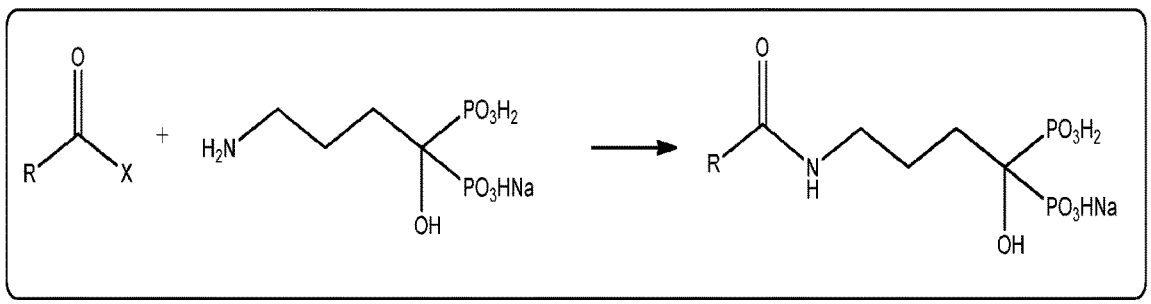
FIG. 2. Synthesis scheme of MA-AL monomer.

The present invention provides, novel Bisphosphonates vinylic monomers and polymers that have utility as biologically active molecule (such as drugs) carriers and for imaging/radiology applications. In one embodiment, the present invention provides a compound comprising formula I:

wherein
X is H, $CH_3$, CN, phenyl or a substituted phenyl, $(CH_2)_mZ$, phenyl$(CH_2)_mZ$;
Y is bisphosphonate, hydroxyl bisphosphonate, phenyl-bisphosphonate, phenyl-hydroxyl bisphosphonate, substituted phenyl-bisphosphonate, Phenyl $(CH_2)_n$ bisphosphonate, or Substituted Phenyl$(CH_2)_n$BP, (polyethylene glycol)$_n$-bisphosphonate, or (Polyethyleneimine)n-bisphosphonate;
Z is CN, $NH_2$, Thiol, OH, or $CO_2H$;
m equals 1 to 20; and
n equals 1 to 200.

In one embodiment, the present invention provides a compound comprising formula II:

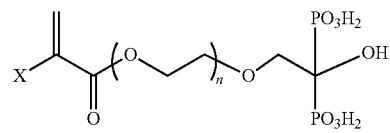

Wherein
X is H, $CH_3$, CN, phenyl or a substituted phenyl, $(CH_2)_mZ$, or phenyl$(CH_2)_mZ$;
m equals 1 to 20;
n equals 1 to 200; and
Z is CN, $NH_2$, Thiol, OH, or $CO_2H$.

In one embodiment, the present invention provides a compound comprising formula III:

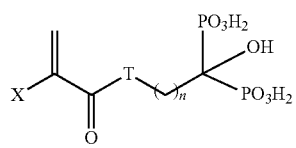

Wherein X is H, $CH_3$, CN, phenyl or a substituted phenyl, $(CH_2)_mZ$, or phenyl$(CH_2)_mZ$;
T is O, N, S, or NH;
m equals 1 to 20;
n equals 1 to 100; and
Z is CN, $NH_2$, Thiol, OH, or $CO_2H$ In one embodiment, the present invention provides a compound comprising formula IV:

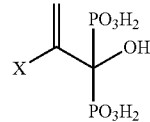

Wherein
X is H, $CH_3$, OH, phenyl, substituted phenyl, $(CH_2)_mZ$, or phenyl$(CH_2)_mZ$;

m equals 1 to 20; and

Z is functional group, such as: CN, NH$_2$, Thiol, OH, or CO$_2$H.

In one embodiment, the present invention provides a compound comprising formula V:

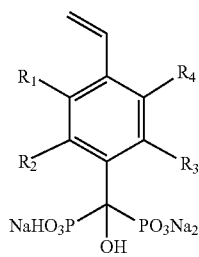

Wherein

R$_1$, R$_2$, R$_3$, and R$_4$ are independently: H, CH$_3$, OH, or a halogen.

In one embodiment, the present invention provides a compound comprising formula VI:

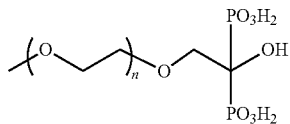

Wherein n equals 1 to 200.

In one embodiment, a compound of the invention such as the compounds comprising formulas I to VI have "n" value between 1 to 5. In another embodiment, a compound of the invention such as the compounds comprising formulas I to VI have "n" value between 3 to 10. In another embodiment, a compound of the invention such as the compounds comprising formulas I to VI have "n" value between 5 to 15. In another embodiment, a compound of the invention such as the compounds comprising formulas I to VI have "n" value between 10 to 100. In another embodiment, a compound of the invention such as the compounds comprising formulas I to VI have "n" value between 5 to 50.

In one embodiment, a compound of the invention such as the compounds comprising formulas I to VI have "m" value between 1 to 5. In one embodiment, a compound of the invention such as the compounds comprising formulas I to VI have "m" value between 2 to 8. In one embodiment, a compound of the invention such as the compounds comprising formulas I to VI have "m" value between 7 to 15. In one embodiment, a compound of the invention such as the compounds comprising formulas I to VI have "m" value between 10 to 20.

In one embodiment, a compound of the invention such as the compounds comprising formulas I to VI are Bisphosphonates (BPs) vinylic monomers. In another embodiment, a compound of the invention such as the compounds comprising formulas I to VI is a Bisphosphonate (BP) vinylic monomer that is further polymerized. In another embodiment, a compound of the invention is a non-hydrolyzable pyrophosphate analogue. In another embodiment, a compound of the invention has high affinity to hydroxyapatite. In another embodiment, a compound of the invention has the ability to create bidentate or tridentate chelates with calcium ions. In another embodiment, a compound of the invention can form strong interactions with dentin, enamel and bones.

In another embodiment, a compound of the invention is a non-biodegradable BP vinylic monomers. In another embodiment, a compound of the invention is a biodegradable BP vinylic monomer. In another embodiment, a polymer of the invention is composed of a single monomer of any one of the compounds disclosed herein. In another embodiment, a polymer of the invention is composed of two or more different monomers of any one of the compounds disclosed herein.

In another embodiment, a BP monomer of the invention and BP polymers comprising or consisting the BP monomer described herein are used for skeletal imaging and therapy, tissue engineering, bone cement, dental applications and metal ions chelation (e.g., Ca, Fe, etc.).

In another embodiment, a BP monomer of the invention to be utilized in a BP polymer is a methacrylamide alendronate monomer (MA-AL). In another embodiment, a BP monomer of the invention to be utilized in a BP polymer is a methacrylate-PEG-alendronate amide monomer (MA-PEG-AL). In another embodiment, a halogen is a halide.

In another embodiment, this invention further provides a polymer or a particle comprising any of the above monomers or any combination of the above monomers. In another embodiment, the particle or polymer further comprises a biologically active molecule.

In another embodiment, vinylic BP monomers of the invention comprising side groups have been prepared by direct conversion of carboxylate group/s of the vinylic monomers to BP. In another embodiment, the obtained BPs vinylic monomers have been used as precursors for the preparation of BPs aqueous soluble small molecules and polymers, and nano and/or micro particles. In another embodiment, vinylic BP polymers and particles comprise biologically active or bioactive reagents (e.g., drugs, antibiotics, etc.) and/or contrast agent/s (e.g., fluorescent dye, magnetic iron oxide or heavy element). In another embodiment, a particle is comprised of a poly composed of any of the compounds disclosed herein. In another embodiment, a monomer, a particle or a polymer comprises a biologically active molecule. In another embodiment, a biologically active molecule is any drug, contrast agent, dye, or a tissue structural support element. In another embodiment, a biologically active molecule is a protein or a small molecule. In another embodiment, a biologically active molecule is a radioisotope. In another embodiment, a biologically active molecule is a fluorescent dye. In another embodiment, a biologically active molecule comprises an amino group.

In another embodiment, a particle of the invention comprises a metallic core or a metal oxide core bound via a reactive group to a compound of the invention. In another embodiment, a particle of the invention is a hollow particle. In another embodiment, a hollow particle is obtained by assembling a particle of the invention comprising a polymeric core and thereafter melting the polymeric core. In another embodiment, a hollow particle is used as a carrier for compounds such as drugs and/or imaging reagents. In another embodiment, and/or imaging reagents occupy the core of the previous hollow particle. In another embodiment, a particle of the invention comprises a drug, a protein, a nucleic acid, and/or imaging reagent core.

In another embodiment, vinylic BP homo and co-polymers are nanoparticles. In another embodiment, vinylic BP polymers or BP polymers are microparticles. In another embodiment, vinylic BP polymers or BP polymers are water soluble. In another embodiment, vinylic BP polymers or BP polymers are water insoluble.

The present novel invention differs from the prior art which discloses, in vivo, coupling of alendronate to a carrier via biodegradable bonds (e.g., ester or amide bonds) while the present invention discloses the novel conversion of a carboxylate group of the precursors to BP via a non-biodegradable bond. In some embodiments, this crucial difference enables the formation of non-biodegradable monomers and polymers.

In one embodiment, novel vinylic monomers comprise in-vivo biodegradable bond/s between the vinylic monomer and the BP moiety (ester or amide bonds). In some embodiments, these in-vivo biodegradable monomers are water soluble and can further be utilized as building blocks for polymers and particles that are in-vivo biodegradable and water soluble.

In one embodiment, novel vinylic monomers comprise in-vivo non-biodegradable bond/s between the vinylic monomer and the BP moiety. In some embodiments, in-vivo non-biodegradable monomers are water soluble and can further be utilized as building blocks for polymers and particles that are in-vivo non-biodegradable and water soluble.

In one embodiment, a vinylic monomer as described herein is further utilized as a precursors for at least one of the following products: aqueous soluble BP small molecules, aqueous soluble homo and co-polymers and nano/micro homo and co-polymeric particles dispersed in an aqueous solution or dried. In another embodiment, a BP compound as described herein comprises a dye (such as a dye used in medical diagnostics), a contrast agent/s (e.g., fluorescent dye, heavy element and/or magnetic ferrofluid), and/or an appropriate therapeutic agent for diagnostics and/or therapy.

In one embodiment, the present invention further provides Polyethylene glycol (PEG) derivatives containing BPs prepared by phosphorylation of terminal carboxylate functional group/s. In another embodiment, PEG derivatives containing BP are di or multi-functional PEG containing BPs. In another embodiment, PEG derivatives containing BP further comprise a dye (such as a dye used in medical diagnostics), a contrast agent/s (e.g., fluorescent dye, heavy element and/or magnetic ferrofluid), and/or an appropriate therapeutic agent for diagnostics and/or therapy.

In one embodiment, the present invention provides that the monomers are aliphatic monomers. In one embodiment, the present invention further provides that the monomers are aromatic monomers. In another embodiment, aromatic monomers are used in dental applications. In another embodiment, ST-BP monomer is a good candidate as dental primer bearing bisphosphonate side group which enable excellent chelating with calcium in hydroxyl apatite and aromatic ring which give strong mechanical properties. In another embodiment, ST-BP polymer is not biodegradable, which is frequently essential for dental applications.

In one embodiment, the present invention further provides that the BP is a derivative of a dye. In one embodiment, the present invention further provides that the BP is a derivative of a dye where one sulfonate group was exchanged for a carboxylic acid followed by phosphorylation of the terminal carboxylate functional group. In one embodiment, the present invention further provides BP is a derivative of a dye prepared by phosphorylation of terminal carboxylate functional group. In one embodiment, the present invention further provides BP is a derivative of a dye used in medical diagnostics. In one embodiment, the present invention further provides BP is a derivative of ICG (indocyanine green).

In another embodiment, the present invention further provides an article such as but not limited to: a film, a sheet, a fiber, a pipe, or any combination thereof comprising a biocompatible material and/or plastic (such as: polyethylene, polypropylene, polyethyleneterphtalate, etc.) core coated with the polymer or nano/micro particles formed from any one of the compounds described herein or any combination of the compounds described herein. In another embodiment, the present invention further provides that a film, a sheet, a fiber, or a pipe is a medical device or a component of a medical device.

Process of Making Vinylic Monomers Containing BPs

In one embodiment, monomers containing BPs have been prepared by converting the carboxylic acid of vinylic-PEG-$CO_2H$ derivatives, e.g., AA-PEG-$CO_2H$ (acrylic-PEG-$CO_2H$) or MA-PEG-$CO_2H$ (methacrylic-PEG-CO2H) into the BP derivatives. In one embodiment, a novel MA-PEG-BP monomer was prepared by oxidation of the terminal hydroxyl of hydroxyl terminated vinylic PEG monomer, followed by chemical conversion to the BP with two equivalents of phosphite (FIG. 3)

Figure 3:
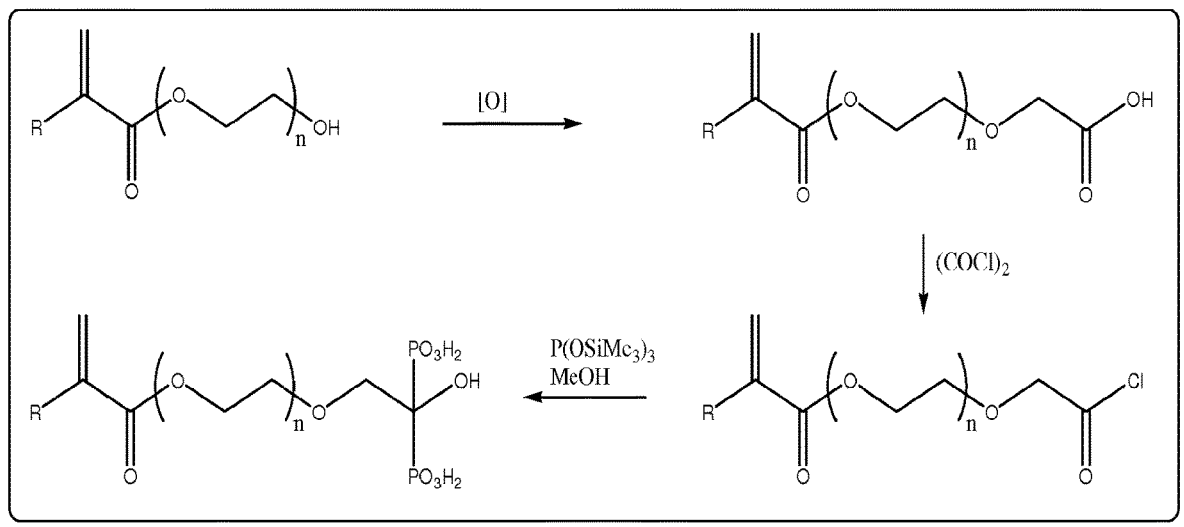
FIG. 3. Synthesis scheme of the MA-PEG-BP monomer formation.

In one embodiment, polymerization is via the R group of the compounds of FIG. 3. In one embodiment, this polymerization site or R group is a vinylic monomer. In one embodiment, this polymerization site or R group is an acrylic acid derivative. In one embodiment, this polymerization site or R group is acrylate (R=CH2=CH), methacrylate (R=CH2=C(Me)), trifluoromethacrylate (R=CH2=C(CF3)); 2-methylenesuccinate (R=CH2=C (CH2CO2H)); or appropriate derivative of styrene (R=CH2=CHPh).

In one embodiment, the number of glycol units in the PEG difunctional monomer may range from n=1 to n=200. In one embodiment, the number of glycol units in the PEG difunctional monomer may range from n=1 to n=50.

Figure 4:
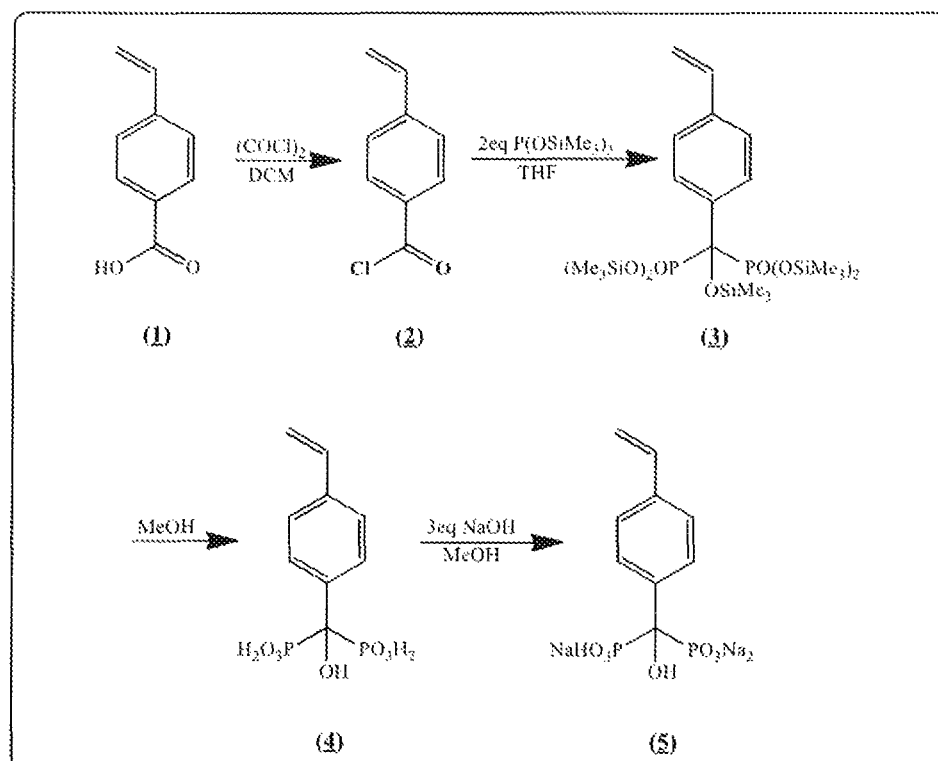
FIG. 4. Synthesis scheme of St-BP monomer.
Figure 5:
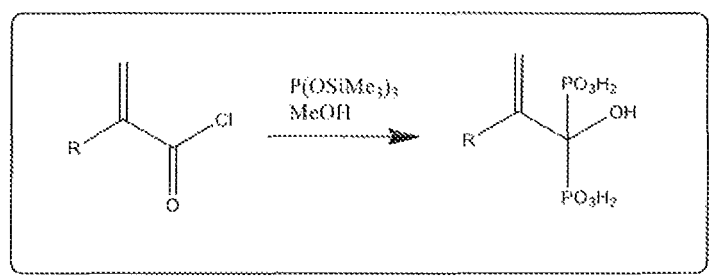
FIG. 5. Synthesis scheme of Acrylate-BPs monomers.

In one embodiment, non-biodegradable vinylic monomer/s containing BPs were obtained by converting the carboxylic acid of vinyl monomers which are not linked to the vinylic double bond via a cleavable or a biodegradable bond, e.g., ester or amide, into a BP. In another embodiment, the vinylic monomer is an acrylate derivative (such as but not limited to: acrylic acid, methyl acrylate, methacrylic acid, methyl methacrylate, etc). In another embodiment, the vinylic monomer is a vinyl benzoic acid derivative (such as but not limited to: 4-vinylbenzoic acid as shown in FIG. 4). In one embodiment, this process resulted in the formation of the following non-biodegradable BPs: acrylic acid BP (AA-BP), methacrylate BP (MA-BP) and trisodium hydroxyl (4-vinylphenyl) methylenebisphosphonic acid (styryl BP, St-BP) (see production scheme for St-BP monomer in FIG. 4; see production scheme for Acrylate-BPs in FIG. 5).

Process of Making Polymers and/or Particles Containing BPs

Figure 6:
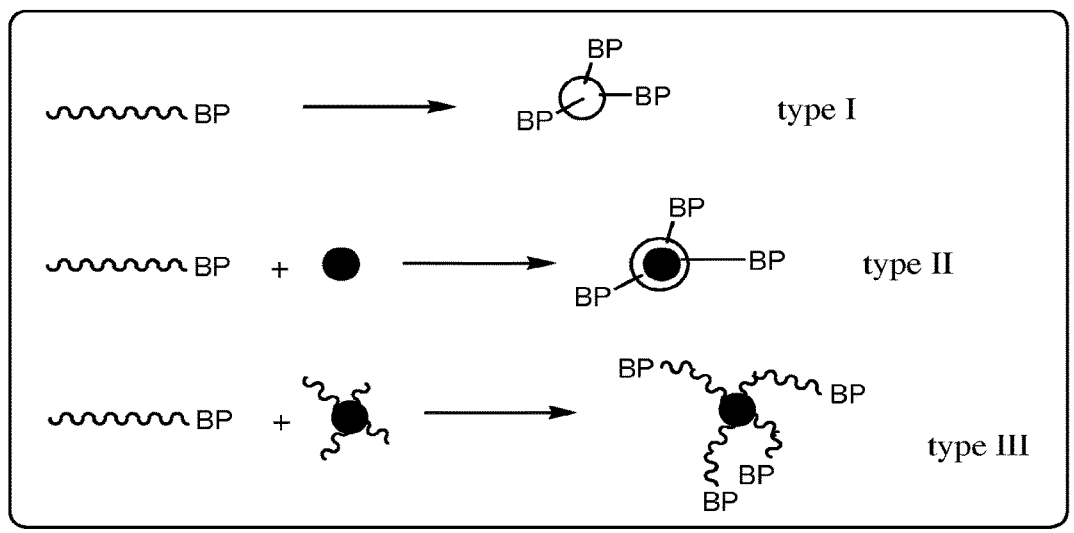
FIG. 6. Synthesis scheme of the three main ways for the preparation of the BPs particles
FIG. 7. Synthesis scheme of ICG-BP(A), and PEG-BP (B).

In one embodiment, particles containing BPs were prepared by heterogeneous co-polymerization of the monomers. In one embodiment, particles containing BPs were prepared by homogeneous co-polymerization of the monomers. In one embodiment, particles containing BPs were prepared by heterogeneous homo or co-polymerization of the monomers, (see FIG. 6 type I).

In another embodiment, these new BPs polymer and/or particles are composed of the novel BPs vinylic monomers of the invention and/or BPs vinylic monomers prepared in other ways, e.g., alendronate methacrylate.

In one embodiment, BPs polymers and/or particles entrap an effecter compound (drug, dye, a photosensitive agent, a compound having a biological activity or chemical activity)

during the polymerization process. In some embodiments, the polymerization process is conducted in the presence of an effecter compound. In some embodiments, the polymerization process is conducted in the presence of particles (e.g. metallic and non-metallic nano/micro-particles). In some embodiments, the polymerization process is conducted in the presence of bioactive molecules, so that the coating BPs polymer entraps the bioactive molecules. In some embodiments, provided herein nano or micro particles having a core and a shell wherein the core comprises an effecter compound, a combination of effecter compounds, a polymer (such as a metal chelating polymer), and/or a metal (see FIG. 6 type II).

In one embodiment, BPs core-shell particles were prepared from the novel BPs vinylic monomers as well as from the BPs vinylic monomers prepared in other ways. In one embodiment, monomers containing BPs are linked to the core (e.g. metallic and non-metallic nano/micro-particles) via reactive groups on the core's surface which may also contain bioactive molecules, such as drugs, photosensitive agents, dyes, etc. (see FIG. 6 type III).

In one embodiment, BPs polymers and/or particles of type I were obtained by free radical heterogeneous homopolymerization of the BP monomers. In one embodiment, BPs polymers and/or particles of type 1 were obtained by free radical heterogeneous copolymerization of the BP monomers. In one embodiment, the obtained homo or co-polymers are water insoluble. In one embodiment, the obtained homo or co-polymers are sparingly water soluble.

In one embodiment, free-radical polymerization process involves the use of an initiator. In another embodiment, free-radical polymerization initiators are well known in the art. In another embodiment, the free-radical polymerization initiator is: persulfate salts, hydrogen peroxide, benzoyl peroxide, azobisizobutyronitrile, azobisizobutyronitrile derivativesazobisizobutyronitrile derivatives, redox initiators, sodium hydrosulfite, hydroperoxide, or any combination thereof. In another embodiment, the free-radical polymerization initiator is a surface bound initiator.

In one embodiment, free-radical polymerization process involves the use of a stabilizer and/or surfactant. In another embodiment, free-radical polymerization stabilizer and/or surfactant are well known in the art. In another embodiment, free-radical polymerization stabilizer and/or surfactant includes but is not limited to: polyvinyl pyrrolidone (PVP), sodium dodecylsulfate (SDS), sodium octylbenzenesulfonate (SOBS), PEG, pluoronics, tween 20, or any combination thereof.

In one embodiment, a vinylic monomer for the preparation of co-polymers includes but is not limited to: MA-PEG (polyethyleneglycol methacrylate), AA-PEG (polyethyleneglycol acrylate), EDMA (ethyleneglycol dimethacrylate), GMA (glycidyl methacrylate), PEGDMA (polyethyleneglycol dimethacrylate), hydroxyethylmethacrylate (HEMA), divinyl benzene, divinylsulfone, methyl methacrylate (MMA), methacrylic acid (MAA) N-(3-Aminopropyl)methacrylamide hydrochloride (APMA), styeren, divinyl benzen (DVB), 4-vinyl benzoic acid, acrylic acid, methacrylic acid, chloromethyl styrene, acrylamide, methacrylamide, acrolein, methacrolein, or any combination thereof.

In one embodiment, the polymerization reaction is carried out by dissolving the monomer(s), initiator/s and stabilizer/surfactant in water. In another embodiment, water is deionized water. In another embodiment, water is purified water. In another embodiment, water is distilled water. In another embodiment, water is at room temperature. In another embodiment, water is lukewarm water. In another embodiment, the water temperature is set for optimum efficiency with respect to nano/micro-particles production.

In another embodiment, monomer(s) are at a concentration in the range of 1-50% (weight % relative to the continuous phase or w/w). In another embodiment, monomer(s) are at a concentration in the range of 1-30%. In another embodiment, monomer(s) are at a concentration in the range of 1-20%. In another embodiment, monomer(s) are at a concentration in the range of 10-30%. In another embodiment, monomer(s) are at a concentration in the range of 5-20%. In another embodiment, monomer(s) are at a concentration in the range of 10-20%.

In another embodiment, initiator(s) are at a concentration in the range of 0.1 to 60% (relative to the weight of the monomer/s). In another embodiment, initiator(s) are at a concentration in the range of 0.25 to 50%. In another embodiment, initiator(s) are at a concentration in the range of 1 to 20%. In another embodiment, initiator(s) are at a concentration in the range of 2.5 to 25%. In another embodiment, initiator(s) are at a concentration in the range of 1 to 15%.

In another embodiment, stabilizer and/or surfactant is/are in the range of 0.1 to 40% (weight % relative to the continuous phase or w/w). In another embodiment, stabilizer and/or surfactant is/are in the range of 0.1 to 20%. In another embodiment, stabilizer and/or surfactant is/are in the range of 0.5 to 20%. In another embodiment, stabilizer and/or surfactant is/are in the range of 2 to 20%.

In another embodiment, after polymerization is completed, the resulting particles or polymers are washed and/or isolated. In another embodiment, after polymerization is completed, the resulting particles or polymers are washed and/or isolated by centrifugation or dialysis. In another embodiment, after polymerization the particles or polymers are dried. In another embodiment, after polymerization the particles or polymers are stored as an aqueous suspension. In another embodiment, the aqueous suspension comprises a buffer. In another embodiment, after polymerization the particles or polymers are stored as an aqueous suspension comprises a stabilizer ((e.g., PVP), to prevent agglomeration).

In one embodiment, BPs polymers and/or particles of type II were obtained by polymerization of BPs monomers, as described above, in the presence of existing particles. As provided hereinabove, in some embodiments, these BPs particles comprise a core-shell structure, wherein the core comprises a particle, a polymer, and/or an effecter compound. An existing particles and the shell is a BP polymer. In some embodiments, the core is dissolved thus obtaining BPs particle-shell. In another embodiment, the core according to polymers and/or particles of type II comprises polystyrene, polymethacrylate, polymethylmethacrylate, polydivinylbenzene polylactic/glycolic, PEG derivatives, proteins such as albumin, polyamino acids, metallic, metal oxide such as zinc oxide, magnesium oxide and iron oxide, etc.

In one embodiment, BPs polymers and/or particles of type III were obtained by conjugation of monomers containing BPs to functional particles. In another embodiment, this conjugation process affords the particles bone or tooth attraction properties. In another embodiment, a particle of the invention is nanoparticle. In another embodiment, a particle of the invention is microparticle.

In another embodiment, the BP monomers are bound together or bound to a particle. In another embodiment, the BP monomers are bound together or bound to a particle via a covalent bond. In another embodiment, the BP monomers are bound together or bound to a particle via an ester, an amide, an anhydride, an ether, a thioether, a disulfide, a sulfonyl ester, a sulfonamide, a C—N bond (via Michael addition reaction), a Si—O bond, a Si—C bond, or any combination thereof.

In another embodiment, the choice of the particular polymerization path has a direct impact on the morphology of the particle. In another embodiment, provided herein aqueous soluble BPs polymers. In another embodiment, provided herein aqueous non-soluble BPs polymers. In another embodiment, provided herein a process of homopolymerizing hydrophilic BP monomers. In another embodiment, provided herein a process of copolymerizing hydrophilic BP monomers and hydrophilic co-vinylic monomer (e.g., PEG acrylate). In another embodiment, water soluble polymers prepared by this invention, are used for the subsequent conjugation of small molecules (drugs, dyes, etc.) In another embodiment, conditions such as polymerization period; lower monomer/s concentrations; various relative concentrations between the monomers involved in co-polymerization processes will determine the identity of the product as provided herein.

In another embodiment, aqueous/water soluble small molecules containing BPs are prepared. In another embodiment, aqueous/water soluble small molecules containing BPs are prepared by Michael addition reaction of the various BP vinylic monomers with appropriate difunctional molecules, e.g., 1, 2-amino thio ethanol. In another embodiment, the interaction was done in physiological pH, so that the thiol group was only added to the double bond within the monomer. In another embodiment, the terminal amino group was further used for binding the BP derivative to a dye or a therapeutic agent.

Figure 7:
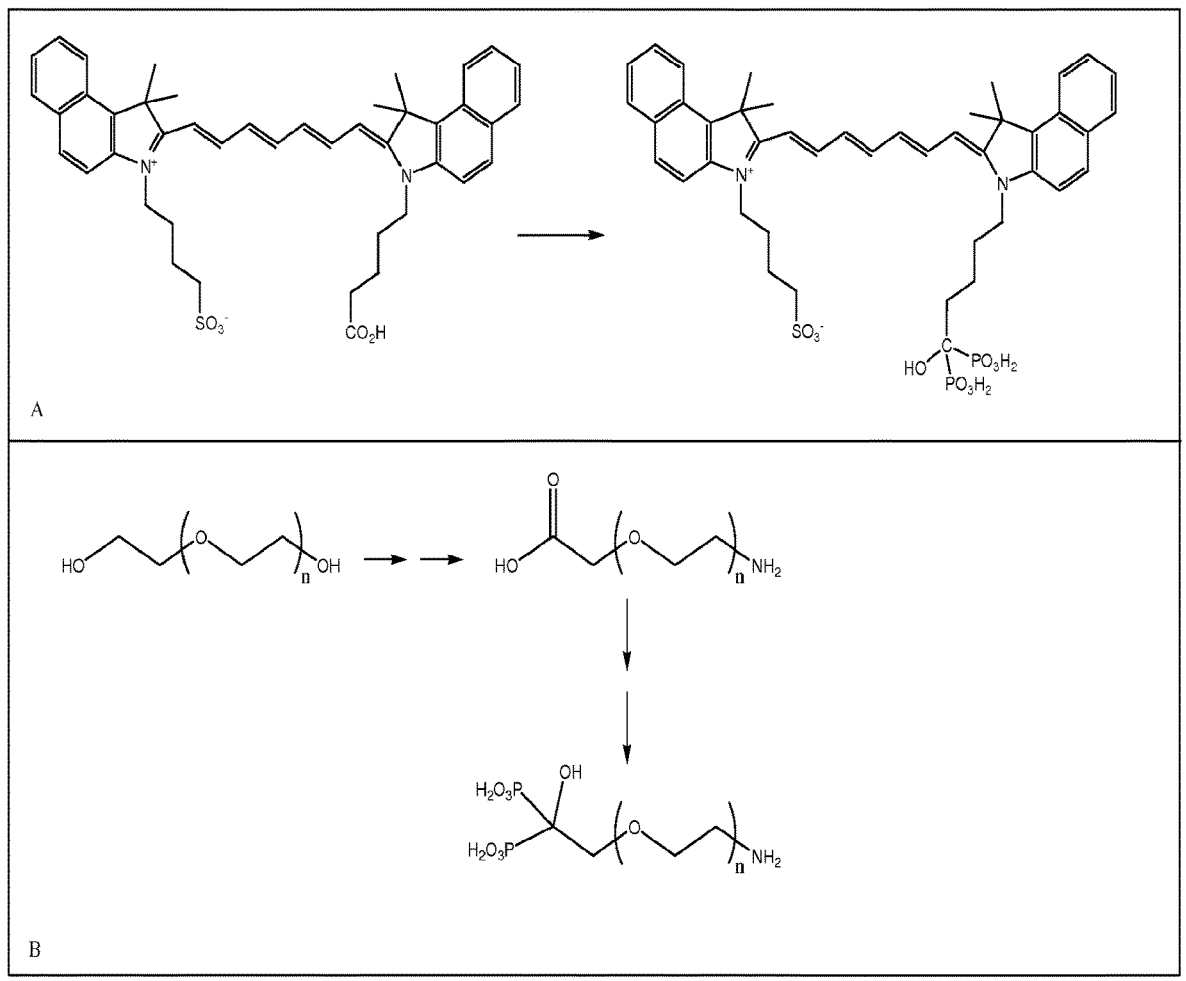

In another embodiment, difunctional molecules were prepared by direct conjugation of a BP to a therapeutic agent or a dye. In another embodiment, a derivative of indocyanine green ((ICG), a near infra-red biocompatible dye) was prepared by exchanging one sulfonate group for a carboxylic acid, Followed by direct conversion of the carboxylate group to BP (thus, a skeleton-targeted near infra-red dye was prepared). In another embodiment, the ICG molecule is utilized in bone or teeth imaging techniques as it accumulates in bones or tooth growth centers (FIG. 7A).

Figure 8:
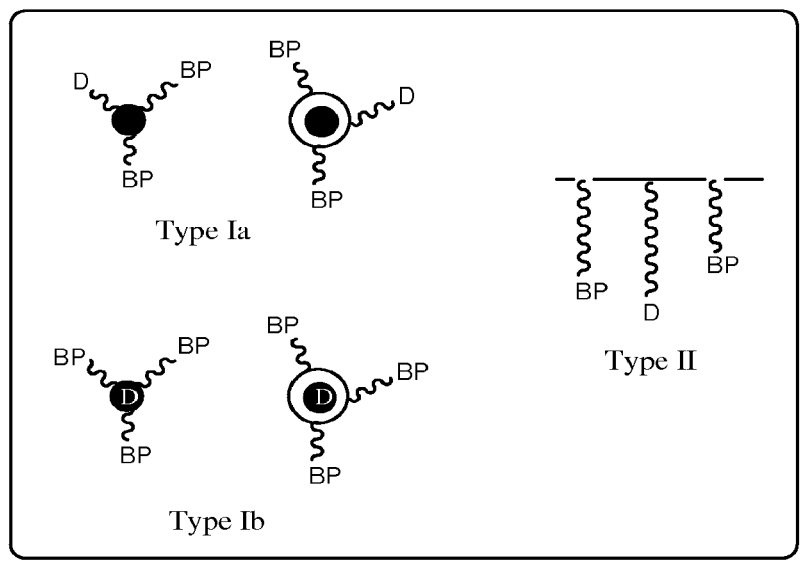
FIG. 8. Scheme showing the binding of bioactive molecules (D) to functional groups on particles (type Ia) or soluble polyBPs (type II), or soluble small BPs, or encapsulation within the BPs particles (type Ib).

In another embodiment, orthogonal difunctional PEG (water soluble small molecules or polymers-depending on the M.W. of the difunctional PEG) are utilized for the preparation of targeted skeletal imaging and/or therapy. In another embodiment, BPs derivatives of acid moiety of functional PEGs, e.g., NH2-PEG-CO2H are prepared by direct conversion of the terminal carboxylate group to BP (FIG. 8). In another embodiment, the terminal amino group is further used for binding bioactive compounds such as fluorescent dye, drugs, antibiotic, etc.

In another embodiment, polymers of the invention (particles, water soluble polymers and small molecules prepared according to this invention) are used for imaging of the teeth and/or bones. In another embodiment, polymers of the invention are particularly effective in imaging area of fast turnover, e.g. young growing bones or teeth, areas of bone tumors and metastases. In another embodiment, dye molecules are further encapsulated within or covalently bound to the BPs polymers. In another embodiment, covalently bound to the BPs polymers is via functional groups present or inserted onto the particles and/or the soluble polymer.

In another embodiment, a "dye" includes a contrast agent including radioactive labeled compounds or isotopes. In another embodiment, a "dye" is a photosensitive compound. In another embodiment, the dye is selected from cyanines, phthalocyanines, chlorines, porphyrins, benzoporphyrins, psoralens, purpurins, fluoron dyes and any other agent that absorbs and emits in the range of 500-1200 nm. In another embodiment, a covalently bound dye molecule is bound via an ester, an amide, an anhydride, an ether, an amine, a thioether, a disulfide, a sulfonyl ester, a sulfonamide, or any combination thereof.

In another embodiment, the invention provides a method of making a particle or a polymer of the invention, comprising the step of free radical homopolymerization or copolymerization of monomers of a compound as described herein in the presence of: (a) a free radical homopolymerization or copolymerization initiator; (b) a free radical homopolymerization or copolymerization stabilizer.

In another embodiment, the reaction mixture for making the particle or polymer of the invention comprises 1-20% by weight of monomers of a compound of the invention. In another embodiment, the reaction mixture for making the particle or polymer of the invention comprises 1-5% by weight of monomers of a compound of the invention. In another embodiment, the reaction mixture for making the particle or polymer of the invention comprises 3-15% by weight of monomers of a compound of the invention. In another embodiment, the reaction mixture for making the particle or polymer of the invention comprises 10-20% by weight of monomers of a compound of the invention. In another embodiment, the reaction mixture for making the particle or polymer of the invention comprises 15-20% by weight of monomers of a compound of the invention. In another embodiment, the reaction mixture for making the particle or polymer of the invention comprises 6-12% by weight of monomers of a compound of the invention.

In another embodiment, the reaction mixture for making the particle or polymer of the invention comprises 0.2-50% by weight of a free radical homopolymerization or copolymerization initiator, e.g., persulfate salts, hydrogen peroxide, benzoyl peroxide, azobisizobutyronitrile, azobisizobutyronitrile derivatives, redox initiators, e.g., sodium hydrosulfite and potassium persulfate. In another embodiment, the reaction mixture for making the particle or polymer of the invention comprises 0.2-5% by weight of a free radical homopolymerization or copolymerization initiator. In another embodiment, the reaction mixture for making the particle or polymer of the invention comprises 1-10% by weight of a free radical homopolymerization or copolymerization initiator In another embodiment, the reaction mixture for making the particle or polymer of the invention comprises 5-20% by weight of a free radical homopolymerization or copolymerization initiator. In another embodiment, the reaction mixture for making the particle or polymer of the invention comprises 15-40% by weight of a free radical homopolymerization or copolymerization initiator. In another embodiment, the reaction mixture for making the particle or polymer of the invention comprises 15-30% by weight of a free radical homopolymerization or copolymerization initiator. In another embodiment, the reaction mixture for making the particle or polymer of the invention comprises 0.2-10% by weight of a free radical homopolymerization or copolymerization initiator.

In another embodiment, the reaction mixture for making the particle or polymer of the invention comprises 0.1-20% by weight of a free radical homopolymerization or copolymerization stabilizer, e.g., polyvinyl pyrrolidone (PVP), sodium dodecylsulfate (SDS), sodium octylbenzenesulfonate (SOBS), PEG, pluoronics, tween 20, or any combination thereof. -*In another embodiment, the reaction mixture for making the particle or polymer of the invention comprises 0.1-5% by weight of a free radical homopolymerization or copolymerization stabilizer. In another embodiment, the reaction mixture for making the particle or polymer of the invention comprises 0.5-10% by weight of a free radical homopolymerization or copolymerization stabilizer. In another embodiment, the reaction mixture for making the particle or polymer of the invention comprises 1-8% by weight of a free radical homopolymerization or copolymerization stabilizer. In another embodiment, the reaction mixture for making the particle or polymer of the invention comprises 5-15% by weight of a free radical homopolymerization or copolymerization stabilizer In another embodiment, the invention further provides that assembly of the particles or polymers of the invention involve a Michael addition reaction including: (a) thiolating a double bond within a compound of the invention; and (b) binding the thiolated compound of the invention to an amino group within a biologically active molecule. In another embodiment, thiolating is accomplished by reacting a compound of the invention with 1, 2-amino-thio-ethanol.

In another embodiment, the invention further provides a method of imaging a bone or tooth in a subject, comprising the step of administering to the subject a composition comprising an effective amount of a particle comprising a dye or a contrast agent. In another embodiment, the invention further provides a method of imaging further comprises irradiating the dye or the contrast agent. In another embodiment, a dye is covalently bound to a compound of the invention. In another embodiment, a dye is physically entrapped within the particle.

In another embodiment, provided herein a method of delivering a biologically active compound to a bone or tooth in a subject, comprising the step of administering to the subject a composition comprising an effective amount of a particle of the invention. In another embodiment, the biologically active compound is covalently bound to the compound of the invention or physically entrapped within a particle of the invention.

In another embodiment, provided herein a method of treating a bone or tooth related disease in a subject, comprising the step of administering to the subject a composition comprising an effective amount of the particle comprising a bone or tooth related disease drug. In another embodiment, the bone or tooth related disease drug is covalently bound to the compound of the invention or physically entrapped within a particle as described herein.

In another embodiment, a bone disease is: bone spurs, bone tumor, chondroblastoma, chondromyxoid, fibroma, enchondroma, an extra-abdominal desmoid tumor, fibrous dysplasia, giant cell tumor of bone, hypophosphatasia, osteoporosis, osteoarthritis, klippel-feil syndrome, limb length discrepancy, osteochondritis dissecans, osteochondroma, osteoid osteoma, osteomalacia, osteopetroses, proteus syndrome, or unicameral bone cyst.

In another embodiment, a bone related disease drug is Alendronate. In another embodiment, a bone related disease drug is Calcitonin. In another embodiment, a bone related disease drug is Raloxifene. In another embodiment, a bone related disease drug is a bone growth factor and/or a bone morphogenetic protein.

Uses

In another embodiment, the polymers and particles of the invention are used as drug carriers for the treatment of bone or tooth infection (osteomyelitis). In another embodiment, the polymers and particles of the invention enable the penetration of drugs into infected bone or tooth sites that are otherwise inaccessible. In another embodiment, the polymers and particles of the invention enable the use of significant lower dosage of a drug treating a bone or a tooth tissue and thus avoid high serum drug levels that are often associated with nephrotoxicity and/or ototoxicity, and can cause gastroinstestinal side effects.

In another embodiment, the polymers and particles of the invention are used as targeted carriers to bones and teeth. In another embodiment, bioactive molecules that can be used according to the present invention include, but are not limited to: Beta lactams such as: penicillin, ampicillin, amoxicillin, penicillin G, carbenicillin, tacarcillin, methicillin, oxacillin, cloxacillin. In another embodiment, bioactive molecules that can be used according to the present invention include, but are not limited to: Cephalosporins such as cefadroxil, cefazolin, cephalexin, cefaclor, cefotetan, cefoxitin, cefprozil, cefuroxime, loracarbef, cefdinir, cefixime, cefoperazone, cefotaxime, cefpodoxime, ceftazidime, ceftibuten, ceftozoxime, ceftriaxone, cefepime, ancef. In another embodiment, bioactive molecules that can be used according to the present invention include, but are not limited to: Aminoglycosides such as: gentamycin, streptomycin, neomycin, lincomycin, kanamycin, vancomycin, sisomycin, tobramycin. In another embodiment, bioactive molecules that can be used according to the present invention include, but are not limited to: Macrolides, polypeptide antibiotics and quinolone antibiotics.

In another embodiment, the polymers and particles of the invention are used in the treatment of malignant bone conditions including bone tumors (osteosarcoma) and metastases originating from tumors in other organs.

In another embodiment, the present invention provides an effective carrier for delivering therapeutic compounds to a bone, tooth, or a skeletal tissue. In another embodiment, the therapeutic compound is an anti-cancer drug, an antibiotic, an osteoclast inhibitor, an anti-inflammatory agent, a bone growth factor, an analgesic, an antibody, a protein, a small molecule or any combination thereof. In another embodiment, the present invention provides an efficient carrier system for in-situ treating any bone or dental pathology. In another embodiment, the present invention provides a bone-targeted carrier for drugs treating bone malignancies.

In another embodiment, the present invention provides an efficient carrier system for resin composite, enamel, dentin, antibiotics, an analgesic, a filler, or primers containing phosphoric acid esters.

In another embodiment, the present invention provides an efficient carrier system for ex-vivo, in-vitro, and in-vivo growth, differentiation, and implantations of cells and cell/tissue scaffolds in a region of bone tissue loss or damage. Polymeric materials, especially phosphonated polymers, already proved to be of great interest in this field. In another embodiment, the present invention provides that novel BPs monomers, degradable and non-degradable, that are precursor for homo-polymer and co-polymer with high phosphonate content are utilized in tissue engineering applications (an optimal phosphonate content induces osteoblast-like cell adhesion and proliferation is obtained).

In another embodiment, the present invention provides the use of the current BPs in the formation of synthetic analogues of bones. In another embodiment, the present invention provides combined compositions comprising poly (sterylbisphosphonates) particles and/or ST-BP monomer and bone cement (the composition of the present invention enhances the mechanical properties of the cement). In another embodiment, the present invention provides the use of the current BPs in the assembly of bone scaffolds. In another embodiment, the present invention provides the use of the current BPs in coating bone scaffolds. In another embodiment, the present invention provides that bone scaffold comprise polymers and/or particles of the invention. In another embodiment, the present invention provides that bone scaffold comprise polymers and/or particles of the invention which comprise (entrap and/or bound) a bone growth factor, an osteoblasts growth factor, a bone morphogenic protein, a dye, a marker, a label, a contrast agent, an anti-inflammatory, an antibiotic or any combination thereof.

In another embodiment, the present invention provides that polymers and/or particles of the invention comprise (entrap and/or bound) a bone growth factor, an osteoblasts growth factor, a bone morphogenic protein, a dye, a marker, a label, a contrast agent, an anti-inflammatory, an antibiotic or any combination thereof. In another embodiment, the present invention provides that bone related medical devices used in orthopedic surgery comprise polymers and/or particles of the invention. In another embodiment, the present invention provides that bone related medical devices used in orthopedic surgery are coated with polymers and/or particles of the invention.

Compositions

In another embodiment, the term "comprise" includes the term "consist" or is replaceable by the term "consist". In one embodiment, the monomers, polymers, and particles of the present invention can be provided to the individual per se. In one embodiment, the monomers, polymers, and particles of the present invention can be provided to the individual as part of a pharmaceutical composition where it is mixed with a pharmaceutically acceptable carrier.

In one embodiment, a "pharmaceutical composition" refers to a preparation of one or more of the active ingredients described herein with other chemical components such as physiologically suitable carriers and excipients. The purpose of a pharmaceutical composition is to facilitate administration of a compound to an organism.

In one embodiment, "active ingredient" refers to the monomers, polymers, and particles combined with bioactive therapeutic agent, a dye, or a contrast agent.

In one embodiment, the present invention provides combined preparations. In one embodiment, "a combined preparation" defines especially a "kit of parts" in the sense that the combination partners as defined above can be dosed independently or by use of different fixed combinations with distinguished amounts of the combination partners i.e., simultaneously, concurrently, separately or sequentially. In some embodiments, the parts of the kit of parts can then, e.g., be administered simultaneously or chronologically staggered, that is at different time points and with equal or different time intervals for any part of the kit of parts. The ratio of the total amounts of the combination partners, in some embodiments, can be administered in the combined preparation. In one embodiment, the combined preparation can be varied, e.g., in order to cope with the needs of a patient subpopulation to be treated or the needs of the single patient which different needs can be due to a particular disease, severity of a disease, age, sex, or body weight as can be readily made by a person skilled in the art.

In one embodiment, the phrases "physiologically acceptable carrier" and "pharmaceutically acceptable carrier" which be interchangeably used refer to a carrier or a diluent that does not cause significant irritation to an organism and does not abrogate the biological activity and properties of the administered monomers, polymers, and particles. An adjuvant is included under these phrases. In one embodiment, one of the ingredients included in the pharmaceutically acceptable carrier can be for example polyethylene glycol (PEG), a biocompatible polymer with a wide range of solubility in both organic and aqueous media (Mutter et al. (1979).

In one embodiment, "excipient" refers to an inert substance added to a pharmaceutical composition to further facilitate administration of monomers, polymers, and particles of the invention. In one embodiment, excipients include calcium carbonate, calcium phosphate, various sugars and types of starch, cellulose derivatives, gelatin, vegetable oils and polyethylene glycols.

Techniques for formulation and administration of drugs are found in "Remington's Pharmaceutical Sciences," Mack Publishing Co., Easton, Pa., latest edition, which is incorporated herein by reference.

In one embodiment, suitable routes of administration, for example, include oral, rectal, transmucosal, transnasal, intestinal or parenteral delivery, including intramuscular, subcutaneous and intramedullary injections as well as intrathecal, direct intraventricular, intravenous, intraperitoneal, intranasal, or intraocular injections.

In one embodiment, the preparation is administered in a local rather than systemic manner, for example, via injection of the preparation directly into a specific region of a patient's body.

Various embodiments of dosage ranges are contemplated by this invention. The dosage of the monomers, polymers, and particles of the invention, in one embodiment, is in the range of 0.05-80 mg/day. In another embodiment, the dosage is in the range of 0.05-50 mg/day. In another embodiment, the dosage is in the range of 0.1-20 mg/day. In another embodiment, the dosage is in the range of 0.1-10 mg/day. In another embodiment, the dosage is in the range of 0.1-5 mg/day. In another embodiment, the dosage is in the range of 0.5-5 mg/day. In another embodiment, the dosage is in the range of 0.5-50 mg/day. In another embodiment, the dosage is in the range of 5-80 mg/day. In another embodiment, the dosage is in the range of 35-65 mg/day. In another embodiment, the dosage is in the range of 35-65 mg/day. In another embodiment, the dosage is in the range of 20-60 mg/day. In another embodiment, the dosage is in the range of 40-60 mg/day. In another embodiment, the dosage is in a range of 45-60 mg/day. In another embodiment, the dosage is in the range of 40-60 mg/day. In another embodiment, the dosage is in a range of 60-120 mg/day. In another embodiment, the dosage is in the range of 120-240 mg/day. In another embodiment, the dosage is in the range of 40-60 mg/day. In another embodiment, the dosage is in a range of 240-400 mg/day. In another embodiment, the dosage is in a range of 45-60 mg/day. In another embodiment, the dosage is in the range of 15-25 mg/day. In another embodiment, the dosage is in the range of 5-10 mg/day. In another embodiment, the dosage is in the range of 55-65 mg/day.

In one embodiment, the dosage is 20 mg/day. In another embodiment, the dosage is 30 mg/day. In another embodiment, the dosage is 40 mg/day. In another embodiment, the dosage is 50 mg/day. In another embodiment, the dosage is 60 mg/day. In another embodiment, the dosage is 70 mg/day. In another embodiment, the dosage is 80 mg/day. In another embodiment, the dosage is 90 mg/day. In another embodiment, the dosage is 100 mg/day.

Oral administration, in one embodiment, comprises a unit dosage form comprising tablets, capsules, lozenges, chewable tablets, suspensions, emulsions and the like. Such unit dosage forms comprise a safe and effective amount of the desired monomers, polymers, and particles of the invention each of which is in one embodiment, from about 0.7 or 3.5 mg to about 280 mg/70 kg, or in another embodiment, about 0.5 or 10 mg to about 210 mg/70 kg. The pharmaceutically-acceptable carriers suitable for the preparation of unit dosage forms for peroral administration are well-known in the art. In some embodiments, tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. In one embodiment, glidants such as silicon dioxide can be used to improve flow characteristics of the powder-mixture. In one embodiment, coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. In some embodiments, the selection of carrier components depends on secondary considerations like taste, cost, and shelf stability, which are not critical for the purposes of this invention, and can be readily made by a person skilled in the art.

In one embodiment, the oral dosage form comprises predefined release profile. In one embodiment, the oral dosage form of the present invention comprises an extended release tablets, capsules, lozenges or chewable tablets. In one embodiment, the oral dosage form of the present invention comprises a slow release tablets, capsules, lozenges or chewable tablets. In one embodiment, the oral dosage form of the present invention comprises an immediate release tablets, capsules, lozenges or chewable tablets. In one embodiment, the oral dosage form is formulated according to the desired release profile of the pharmaceutical active ingredient as known to one skilled in the art.

Peroral compositions, in some embodiments, comprise liquid solutions, emulsions, suspensions, and the like. In some embodiments, pharmaceutically-acceptable carriers suitable for preparation of such compositions are well known in the art. In some embodiments, liquid oral compositions comprise from about 0.012% to about 0.933% of the desired compound or compounds, or in another embodiment, from about 0.033% to about 0.7%.

In some embodiments, compositions for use in the methods of this invention comprise solutions or emulsions, which in some embodiments are aqueous solutions or emulsions comprising a safe and effective amount of the compounds of the present invention and optionally, other compounds, intended for topical intranasal administration. In some embodiments, h compositions comprise from about 0.01% to about 10.0% w/v of a subject compound, more preferably from about 0.1% to about 2.0, which is used for systemic delivery of the compounds by the intranasal route.

In another embodiment, the pharmaceutical compositions are administered by intravenous, intra-arterial, or intramuscular injection of a liquid preparation. In some embodiments, liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterially, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds of the present invention are combined with an additional appropriate therapeutic agent or agents, prepared and applied as solutions, suspensions, or emulsions in a physiologically acceptable diluent with or without a pharmaceutical carrier.

In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

In one embodiment, pharmaceutical compositions for use in accordance with the present invention is formulated in conventional manner using one or more physiologically acceptable carriers comprising excipients and auxiliaries, which facilitate processing of the active ingredients into preparations which, can be used pharmaceutically. In one embodiment, formulation is dependent upon the route of administration chosen.

In one embodiment, injectables, of the invention are formulated in aqueous solutions. In one embodiment, injectables, of the invention are formulated in physiologically compatible buffers such as Hank's solution, Ringer's solution, or physiological salt buffer. In some embodiments, for transmucosal administration, penetrants appropriate to the barrier to be permeated are used in the formulation. Such penetrants are generally known in the art.

In one embodiment, the preparations described herein are formulated for parenteral administration, e.g., by bolus injection or continuous infusion. In some embodiments, formulations for injection are presented in unit dosage form, e.g., in ampoules or in multidose containers with optionally, an added preservative. In some embodiments, compositions are suspensions, solutions or emulsions in oily or aqueous vehicles, and contain formulatory agents such as suspending, stabilizing and/or dispersing agents.

The compositions also comprise, in some embodiments, preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise, in some embodiments, local anesthetics or other actives. The compositions can be used as sprays, mists, drops, and the like.

In some embodiments, pharmaceutical compositions for parenteral administration include aqueous solutions of the active preparation in water-soluble form. Additionally, suspensions of the active ingredients, in some embodiments, are prepared as appropriate oily or water based injection suspensions. Suitable lipophilic solvents or vehicles include, in some embodiments, fatty oils such as sesame oil, or synthetic fatty acid esters such as ethyl oleate, triglycerides or liposomes. Aqueous injection suspensions contain, in some embodiments, substances, which increase the viscosity of the suspension, such as sodium carboxymethyl cellulose, sorbitol or dextran. In another embodiment, the suspension also contain suitable stabilizers or agents which increase the solubility of the active ingredients to allow for the preparation of highly concentrated solutions.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

In another embodiment, the pharmaceutical composition delivered in a controlled release system is formulated for intravenous infusion, implantable osmotic pump, transdermal patch, liposomes, or other modes of administration. In one embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

In some embodiments, the monomers, polymers, and particles of the invention are in powder form for constitution with a suitable vehicle, e.g., sterile, pyrogen-free water based solution, before use. Compositions are formulated, in some embodiments, for atomization and inhalation administration. In another embodiment, compositions are contained in a container with attached atomizing means.

In one embodiment, the preparation of the present invention is formulated in rectal compositions such as suppositories or retention enemas, using, e.g., conventional suppository bases such as cocoa butter or other glycerides.

In some embodiments, pharmaceutical compositions suitable for use in context of the present invention include compositions wherein the active ingredients are contained in an amount effective to achieve the intended purpose. In some embodiments, a therapeutically effective amount means an amount of active ingredients effective to prevent, alleviate or ameliorate symptoms of disease or prolong the survival of the subject being treated.

In one embodiment, determination of a therapeutically effective amount is well within the capability of those skilled in the art.

The compositions also comprise preservatives, such as benzalkonium chloride and thimerosal and the like; chelating agents, such as edetate sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions also comprise local anesthetics or other actives. The compositions can be used as sprays, mists, drops, and the like.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the Tween™ brand emulsifiers; wetting agents, such sodium lauryl sulfate; coloring agents; flavoring agents; tableting agents, stabilizers; antioxidants; preservatives; pyrogen-free water; isotonic saline; and phosphate buffer solutions. The choice of a pharmaceutically-acceptable carrier to be used in conjunction with the compound is basically determined by the way the compound is to be administered. If the subject compound is to be injected, in one embodiment, the pharmaceutically-acceptable carrier is sterile, physiological saline, with a blood-compatible suspending agent, the pH of which has been adjusted to about 7.4.

In addition, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmellose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, cellulose (e.g. Avicel™, RC-591), tragacanth and sodium alginate; typical wetting agents include lecithin and polyethylene oxide sorbitan (e.g. polysorbate 80). Typical preservatives include methyl paraben and sodium benzoate. In another embodiment, peroral liquid compositions also contain one or more components such as sweeteners, flavoring agents and colorants disclosed above.

The compositions also include incorporation of the monomers, polymers, and particles of the invention into or onto particulate preparations of polymeric compounds such as polylactic acid, polyglycolic acid, hydrogels, etc, or onto liposomes, microemulsions, micelles, unilamellar or multi-lamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In some embodiments, compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. In another embodiment, the modified compounds exhibit substantially longer half-lives in blood following intravenous injection than do the corresponding unmodified compounds. In one embodiment, modifications also increase the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the monomers, polymers, and particles described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

EXAMPLES

Chemicals and Materials

The following analytical-grade chemicals were purchased from commercial sources and used without further purification: poly(ethylene glycol)methacrylate (MA-PEG-OH, m.w. 360), tetra(ethylene glycol) diacrylate (TTEGDA), O—[(N-succinimidyl)succinyl-aminoethyl]-O'-methylpolyethylene glycol (PEG-NHS, m.w. 750), tris(trimethylsilyl) phosphite, Alendronate, potassium persulfate (PPS), 4,4'-azobis(4-cyanovaleric acid) (AIBN-COOH), polyvinylpyrrolidone (PVP, m.w. 360K and 40K), chromium oxide, oxalyl chloride, Triton-x-100, activated charcoal, anhydrous methanol, anhydrous dichloromethane, anhydrous tetrahydrofuran, chloroform, acetone, anhydrous N,N-dimethylformamide (DMF), anhydrous dimethyl sulfoxide (DMSO), sulfuric acid (99%), hydroxyapatite (HAP) and Sephadex LH-20 from Sigma (Rehovot, Israel); N-(3-aminopropyl) methacrylamide hydrochloride (APMA) from Polysciences (Warrington, Pa., USA); 2-morpholino ethanesulfonic acid (MES, pH 6) from Fisher Scientific, USA; Dulbecco's modification of eagle's medium (DMEM), Fetal Bovine Serum (FBS), Phosphate Buffered Saline (PBS, 0.1M pH 7.4), 1% glutamine, 1% penicillin/streptomycin and mycoplasma detection kit from Biological Industries (Bet Haemek, Israel); Bicarbonate Buffer (BB, 0.1M pH 8.4) from Bio-Lab Ltd (Jerusalem, Israel); cytotoxicity detection kit from Roche Diagnostics, USA; Cy7-NHS ester from Lumiprobe (Hallandale beach, FL, USA); cell cytotoxicity assay kit (LDH) from Roche (Switzerland). Water was purified by passing deionized water through an Elgastat Spectrum reverse osmosis system (Elga Ltd., High Wycombe, UK).

Example 1: Preparation of Methacrylamide Alendronate Monomer (MA-AL)

MA-AL monomer was prepared according to Rayment et al. Briefly, Methacryloyl chloride (0.015 mol) was added simultaneously with a solution of NaOH (0.015 mol) in dist. water (10 ml), to an ice-cold solution of alendronate monosodium salt trihydrate (0.01 mol) and NaOH (0.03 mol) in dist. water (20 ml), containing p-methoxy phenol (20 mg, polymerization inhibitor). The mixture was stirred at <5° C. for 1 h and allowed to warm to RT for another 2 h. The mixture was acidified with conc. HCl to pH=2 and washed successively with chloroform to remove excess methacrylic acid. The aqueous solution was neutralized and lyophilized to afford the amide as a white powder.

Example 2: Preparation of Methacrylate-PEG-alendronate Amide Monomer (MA-PEG-AL)

Preparation of Methacrylate-PEG-NHS

N-hydroxysuccinimide (2.1 mmol) was added to a solution of methacrylate-PEG-carboxylic acid (2 mmol) in dry dichloromethane (8 ml), followed by a solution of dicyclohexylcarbodiimide (2.1 mmol) in dry dichloromethane (2 ml) and heavy precipitation occurred. The mixture was stirred at room temperature (RT) overnight. The resulting mixture was filtered and the filtrate evaporated to dryness to give the desired product as thick oil. 1H NMR (CDCl3): δ 1.95 (Bs, 3H, Me-acrylate), 2.86 (s, 4H, COCH2CH2CO), 3.65 (Brs, 16H, OCH2CH2O), 3.75 (m, 4H, OCH2), 4.30 (dd, J=4.8 Hz, 2H, CH2O2C-acrylate), 4.53 (s, 2H, OCH2CO—NHS), 5.58 (m, 1H, CH2=C), 6.13 (m, 1H, CH2=C). 13C NMR (CDCl3): δ 18.27 (Me-acrylate), 25.40 (COCH2CH2CO), 66.49 (OCH2CO), 63.72, 68.94, 70.37 and 71.14 (OCH2CH2O), 125.69 (CH2=C).

Preparation of MA-PEG-AL

A solution of alendronate monosodium salt trihydrate (2 mmol) in dist. water (5 ml) containing NaOH (up to the point of complete alendronate dissolution) was added to a solution of MC-PEG-NHS (2 mmol) in dist. water (3 ml). Precipitation occurred. Stirring was continued at RT for 2 days. The resulting mixture was filtered to give a gummy off-white precipitate and turbid filtrate, which was lyophilized to give the amide as an off-white powder. 1H NMR (D2O): δ 1.80 (m, 2H CH2CH2C(OH)(PO3)2), 1.94 (s, 3H, Me), 2.05 (m, 2H, CH2C(OH)(PO3)2), 3.06 (t, J=6.1 Hz, 2H, CH2N), 3.71 (s, 20H, OCH2CH2O), 3.84 (Brt, J=4 Hz, 2H, CH2CH2CO2), 4.09 (s, 2H, OCH2CON), 4.35 (Brt, J=4 Hz, 2H, CH2CO2), 5.74 (m. 1H, CH2=C), 6.16 (m, 1H, CH2=C). 13C NMR (D2O): δ 17.33 (Me), 22.34 (t, JP-C—C=7 Hz, CH2C(OH)(PO3)2), 30.84 (CH2CH2N), 39.97 (CH2N), 64.10, 68.46, 69.51, 69.66 and 70.17 (OCH2CH2O), 73.77 and 73.52 (two t, JP-C=129 Hz, C(OH)(PO3)2), 126.92 (CH2-vinyl), 135.71 (C-vinyl), 172.20 (CO-vinyl), 179.23 (CON). 31P NMR (D2O): δ 18.696 and 19.012.

TOF MS ES+: MNa+ PEG series: 617 ([MNa]+, n=5, 5%), 573 ([MNa]+, n=4, 7%), 529 ([MNa]+, n=3, 8%). MNa+ PEG-NH2 series (loss of alen chain): 607 ([MNa]+, n=10, 5%), 563 ([MNa]+, n=9, 15%), 519 ([MNa]+, n=8, 30%), 475 ([MNa]+, n=7, 55%), 431 ([MNa]+, n=6, 80%), 387 ([MNa]+, n=5, 90%), 343 ([MNa]+, n=4, 55%), 299 ([MNa]+, n=3, 20%), 255 ([MNa]+, n=2, 5%). MNa+ PEG=NH series (loss of alen chain): 530 ([MNa]+, n=8, 5%), 486 ([MNa]+, n=7, 30%), 442 ([MNa]+, n=6, 70%), 398 ([MNa]+, n=5, 100%), 354 ([MNa]+, n=4, 95%), 310

([MNa]+, n=3, 45%), 266 ([MNa]+, n=2, 10%). TOF MS ES–: M– PEG series: 638 (M–, n=6, 5%), 594 (M–, n=5, 12%), 550 (M–, n=4, 25%), 506 (M–, n=3, 27%), 462 (M–, n=2, 35%), 418 (M–, n=1, 30%), 374 (M–, n=0, 20%).

Example 3: Preparation of MA-PEG-BP Monomer

MA-PEG-CO2H (750 mg, 2 mmol) was dissolved in dry dichloromethane (5 ml). DMF (1 drop) was added as catalyst, followed by oxalyl chloride (340 μL, 4 mmol, 2 eq.). Gas evolution was observed, the mixture was stirred at rt overnight and gradually turned orange. The resulting mixture was evaporated to dryness, yielding orange oil which was dissolved in THF (5 ml). Tris(trimethylsilyl)phosphite (1.34 ml, 4 mmol, 2 eq.) was added and the mixture was stirred at rt for 1 h. The mixture was evaporated to dryness, then methanol (5 ml) was added and the dark mixture was stirred overnight at room temperature (rt). The mixture was again evaporated. The residue solidified upon standing. 1H, 31P and 13C NMR showed the desired product (MA-PEG-BP monomer, FIG. 3). 1H NMR (CD3OD): δ 1.94 (s, 3H, Me), 3.64 (Brs, 22H, (CH2CH2O)), 3.73 (m, 2H, CH2CH2OCO), 3.87 (s, 2H, OCH2C(PO3H2)2), 4.29 (m, 2H, CH2OCO), 5.65 (s, 1H, vinyl), 6.12 (s, 1H, vinyl).

Example 4: Preparation of the Styryl BP Monomer—Trisodium hydroxyl (4-vinylphenyl) methelenebisphosphonic acid [St-BP]

4-vinylbenzoic acid (2.0 g, 13.5 mmol) was dissolved in dry dichloromethane (50 ml) at room temperature under nitrogen atmosphere. DMF (1 drop) was added as catalyst, followed by oxalyl chloride (3.0 ml). Gas evolution was observed and the reaction mixture was stirred at room temperature overnight. The resulting mixture (light yellow) was evaporated to dryness yielding clear—yellow oil.

The obtained 4-vinylbenzoyl chloride was dissolved in dry THF (50 ml) and Tris (trimethylsilyl) phosphite (10.0 ml) was added drop wise at room temperature. The reaction mixture was stirred overnight at room temperature and was evaporated to dryness yielding yellowish solid.

The obtained pentakis(trimethylsilyl) hydroxyl (4-vinylphenyl) methylenebisphosphonate was taken up in 20 ml of absolute dry methanol, followed immediately by the addition of filtered solution of sodium hydroxide (1.62 g, 40.5 mmol) in methanol (40 ml). The flask of the sodium hydroxide methanol solution and the filter paper were washed with another amount of dry methanol (10 ml). The reaction mixture was stirred for 2 h at room temperature. The product was collected by filtration washed with methanol and dried in a desiccators containing phosphorus pentaoxide under vacuum (2 mm Hg) for 4 h. The dried product was get as white powder to give 4.8 g of the product (88%).

IR (neat): 3629 (v, OH), 3000-3100 (s, p-di-substitute aromatic ring CH, CH=CH), 1 631 (s, CH=CH), 1 508 (s, aromatic ring) 1 402 (s, OH) 1 174, 1093(antisymmetric stretch PO3-) 970, 918 (symmetric stretch PO3-) 827 (bend para di-substitute aromatic ring), 742 (s, P—C) 632 552 462 (bend PO3-). 31P NMR (D2O): δ 16.3 ppm (trisodium salt). 1H NMR (D2O): δ 7.76 (d, 2H, aromatic ortho to double bond, 3J=8.0 Hz), 7.48 (d, 2H, aromatic metha to double bond, 3J=8.0 Hz), 6.81 (dd, 1H, 3J trans=11.0 Hz, 3J cis=17.6 Hz), 5.87 (d, 1H, CH2=CH trans to aromatic ring, 3J=17.6 Hz), 5.29 (d, 1H, CH2=CH cis to aromatic ring, 3J=10.8 Hz). 13C NMR (D2O): δ 140.12 (1C, C quaternary near the bisphosphonate group), 136.67 (1C, =CH-aromatic ring), 134.84 (1C, C quaternary near the double bond), 126.37 (2C, aromatic ring ortho to the double bond), 125.1 (2C, aromatic ring metha to the double bond), 113.33 (1C, CH2=CH), 77.53 (t, 1C, C—OH, 2JCP=501 Hz).

TOF MS ES–: 293 (M-3Na, 100%); 315 (M-2Na, 64%). HRMS MALDI: 292.994.

Example 5: Preparation of Methacrylate BP Monomer (MA-BP)

Methacryloyl chloride (0.512 mmol) dissolved in THF (5 ml) containing p-methoxy phenol (1 mg, polymerization inhibitor). Tris(trimethylsilyl)phosphite (341 μL, 1.024 mmol, 2 eq.) was added and the mixture was stirred at RT for 3 h. The mixture was than evaporated to dryness, then methanol (5 ml) was added and the dark mixture was stirred overnight at rt. The mixture was again evaporated. The residue solidified upon standing. 1H, 31P and 13C NMR showed desired product.

Example 6: Preparation of Acrylate BP Monomer (AA-BP)

Acrylate BP (AA-BP) monomer was prepared as described in example 5, substituting the methacryloyl chloride for acryloyl chloride.

Example 7: Synthesis of Crosslinked P(MA-PEG-BP) Nano/Micro Particles

Figure 9:
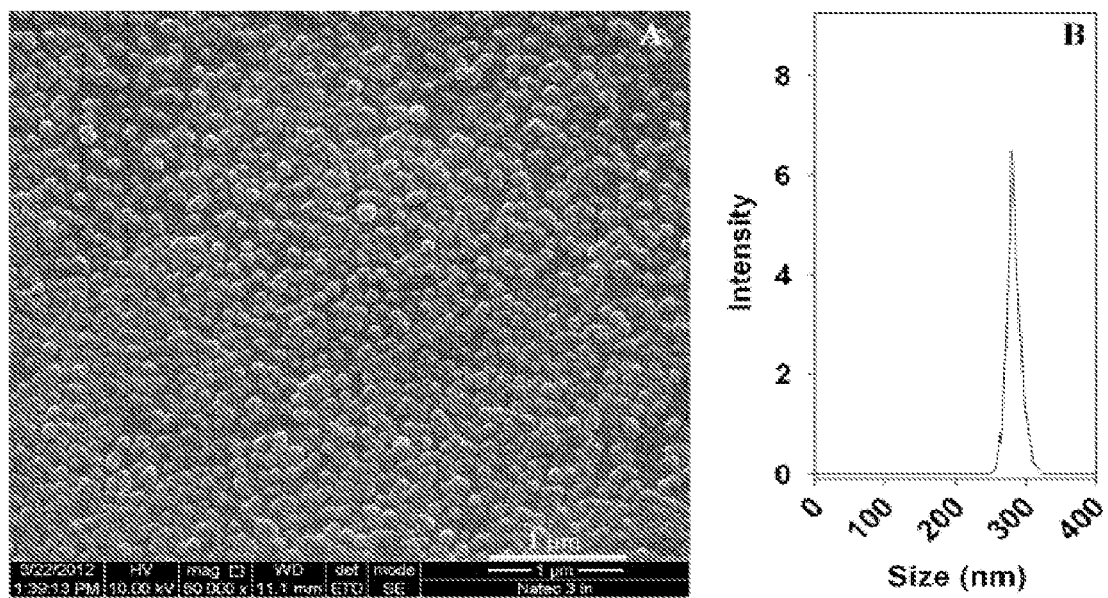
FIG. 9. Depicts SEM image (A) and hydrodynamic size histogram (B) of the crosslinked P(PEG-BP) nanoparticles.

Poly(MA-PEG-BP), P(MA-PEG-BP), particles of 280±22 nm (FIG. 9) were prepared by dispersion polymerization. Briefly, 45 mg of MA-PEG-BP monomer, 45 mg of APMA co-monomer (N-(3-Aminopropyl)methacrylamide hydrochloride) and 10 mg of the crosslinker monomer EDMA were added to a vial containing 2 ml of 0.1 M MES buffer (pH 6) with 8 mg of PPS as initiator and 20 mg of PVP 360K as stabilizer. For the polymerization, the vial containing the mixture was purged with nitrogen gas to exclude air and then was shaken at 83° C. for 24 h. The resulting particles were washed of excess reagents by extensive dialysis cycles with water.

The dry diameter of the BP nanoparticles used in the present work was 138±15 nm, as illustrated by the typical SEM photomicrograph shown in FIG. 9A. The hydrodynamic diameter of these nanoparticles dispersed in water was 280±22 nm, as illustrated by light scattering measurements, as shown in FIG. 9B.

Particles of sizes ranging from about 40 nm up to a few microns were formed by changing various polymerization parameters, e.g., monomers concentration, co-monomer to MA-PEG-BP weight ratio, stabilizer/surfactant type and concentration, polymerization time, polymerization temperature, etc.

Crosslinked bioactive P(MA-PEG-BP) nanoparticles were formed by two possible ways: (1) A similar polymerization process in the presence of the bioactive reagent, e.g., methotrexate, so that the cancer drug was entrapped within these biodegradable BPs particles; (2) Covalent binding of the bioactive reagents to the surface of the BPs particles, e.g., methotrexate via its carboxylate group, to the amino groups of the P(MA-PEG-BP) particles.

Example 8: Grafting of P(MA-PEG-BP) onto PS Particles

Figure 10:
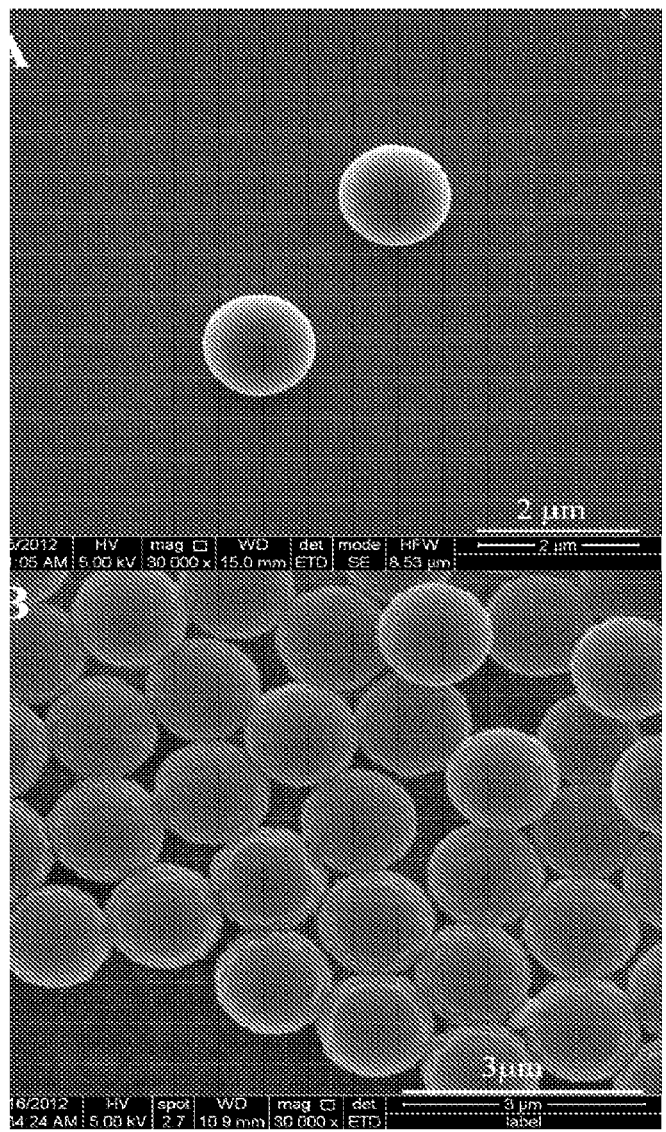
FIG. 10. Depicts SEM photomicrographs of the PS core particles (A) and the P(MA-PEG-BP)/PS core-shell particles (B).

Grafting of P(MA-PEG-BP) polymeric chains onto PS particles of 1.55±0.05 μm were prepared by adding 100 mg MA-PEG-BP, 8 mg PPS, and 0.05 g SDS in 1.5 ml water to 1 ml of an aqueous dispersion of the PS microspheres (150 mg) of 1.37±0.07 µm. The total volume of water is therefore 2.5 ml and the MA-PEG-BP, PPS, SDS concentration are 4% (Vmonomer/V), 8% (w/wmonomer) and 1% (W/V), respectively. For the polymerization of the MA-PEG-BP, the vial containing the above mixture was purged with nitrogen to exclude air and then was shaken at 83° C. for 18 h. The resulting P(MA-PEG-BP) grafted particles were washed off excess reagents, including non-grafted PEG-BP polymeric chains, by several centrifugation cycles with water. FIG. 10 shows SEM pictures of the PS microspheres dispersed in an aqueous continuous phase before (A) and after (B) the grafted dispersion polymerization of the above monomers. FIG. 10A illustrates the smooth surface morphology and perfect spherical shape of the PS microspheres. The measured dried diameter and size distribution of these microspheres are 1.37±0.07 µm. FIG. 10B demonstrates that due to the coating of the PS particles with the P(MA-PEG-BP) the diameter of these particles increased from 1.37±0.07 to 1.55±0.05 µm, so that the coating thickness of the crosslinked P(MA-PEG-BP) is of 0.18±0.02 µm. The surface of the P(MA-PEG-BP) grafted PS particles compared to the PS particles possess bumpy surfaces, as illustrated in FIG. 10B. This bumpy morphology is probably due to the coating of the P(MA-PEG-BP) polymeric chains onto the smooth surface of the PS microspheres.

Figure 11:
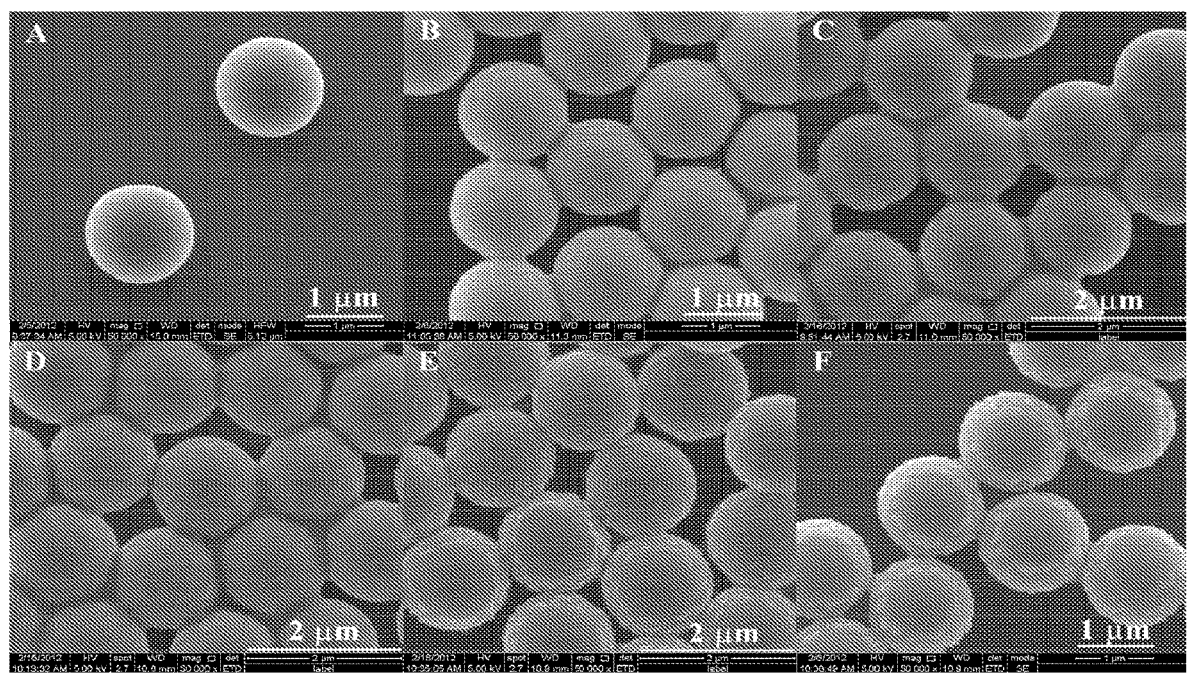
FIG. 11. Depicts SEM photomicrographs of the PS core microspheres (A) and the P(MA-PEG-BP)/PS core-shell microspheres prepared by dispersion polymerization of increasing MA-PEG-BP concentrations, 12.5 (B), 25 (C), 50 (D), 100 (E) and 200 (F) mg, in the presence of the PS microspheres of 1.37±0.07 μm diameter.

The effect of MA-PEG-BP concentration was also examined. FIG. 11 shows SEM photomicrographs of the PS particles (A) and the P(MA-PEG-BP) grafted PS particles produced by the dispersion polymerization of increasing amounts of MA-PEG-BP (12.5, 25, 50, 100, and 200 mg) in the presence of the PS microspheres. These pictures clearly illustrate that increasing the MA-PEG-BP concentration results in increasing size while retaining, more or less, the size distribution of the produced P(MA-PEG-BP) grafted particles. For example, in the presence of 12.5, 25, 50, 100, and 200 mg, the particles' diameter increased from 1.38±0.06 to 1.42±0.12, 1.44±0.11, 1.46±0.17 and 1.5±0.11 respectively. FIG. 11 shows by the SEM photomicrograph that in the presence of a relatively low concentration of MA-PEG-BP e.g., 12.5 mg (FIG. 11B), the P(MA-PEG-BP) coating is composed of discontinuous islands around the PS core particles. FIG. 11C demonstrates, on the other hand, that in the presence of increasing concentration of MA-PEG-BP, e.g., 25 mg, bumpy surfaces composed of continuous coating of P(MA-PEG-BP) on the PS particles were produced. FIGS. 11D, 11E and 11F shows that in the presence of higher MA-PEG-BP concentrations the coating thickness on the PS particles increases.

Similar results were obtained when the PPS and the PS particles were replaced with PS microspheres containing surface hydroperoxides. These P(MA-PEG-BP) coated PS particles can be prepared in sizes ranging between approximately 40 nm to few microns depending on the diameter of the PS core particles and the polymerization conditions. The PS core particles of this invention may also be replaced by other core particles such as polydivinyl benzene and PMMA nano/micro particles. The BP monomer MA-PEG-BP can also be replaced by the other BP monomers. In addition, the nano/micro particles can be replaced with polymers (plastics) of other shape, e.g., films, sheets, pipes, fibers from polypropylene, polyethylene. polyethyleneterphthalate, polystyrene, etc.) and metal or metal oxides, e.g., Ti, $TiO_2$, $SiO_2$, Au, etc.

Example 9: Preparation of Crosslinked P((MA-PEG-BP)/PS Core-shell Micrometer-sized Particles Crosslinked P(MA-PEG-BP)/PS micrometer-sized core-shell particles were prepared by a procedure similar to that described in the previous example, substituting the MA-PEG-BP for a mixture containing both MA-PEG-BP and EDMA. In a typical experiment, crosslinked P(MA-PEG-BP))/PS core-shell particles of an average diameter of 1.57±0.05 µm were prepared by polymerization of 70 mg MA-PEG-BP and 30 µm EDMA in the presence of the PS core microspheres, according to the former procedure.

The core-shell particles formed were then washed by extensive centrifugation cycles with water, and then dried by lyophilization.

Figure 12:
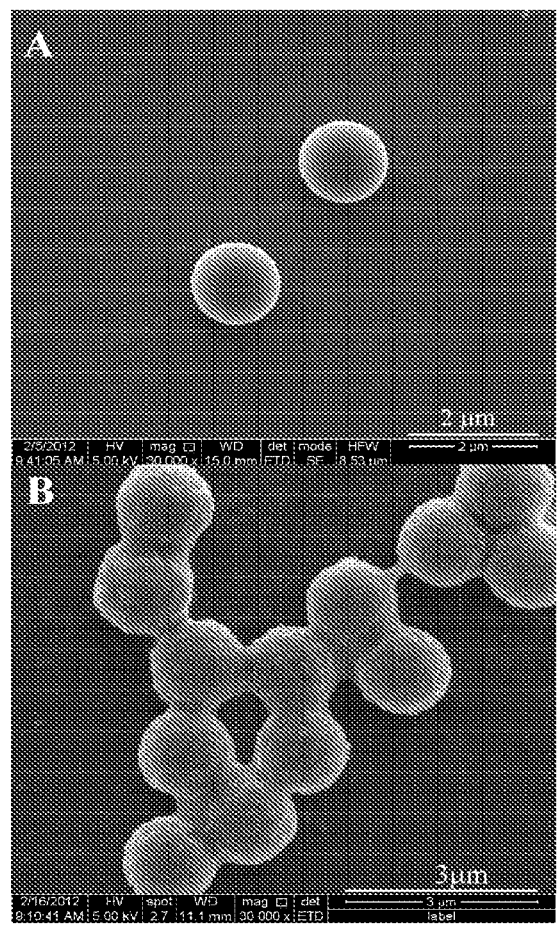
FIG. 12. Depicts SEM photomicrographs of the PS core particles (A) and the crosslinked P(MA-PEG-BP)/PS core-shell particles (B)

P(MA-PEG-BP)/PS core-shell particles of various properties were prepared by changing the monomers ([MA-PEG-BP]/[EDMA]) weight ratio while maintaining the total volume of the monomers to be 100 mg. FIG. 12 shows SEM pictures of the PS microspheres dispersed in an aqueous continuous phase before (A) and after (B) the seeded dispersion polymerization of 50 mg MA-PEG-BP and 50 mg EDMA. FIG. 12A illustrates the smooth surface morphology and perfect spherical shape of the PS microspheres. The measured dried diameter and size distribution of these microspheres are 1.37±0.07 µm. FIG. 12B demonstrates that due to the coating of the PS particles with the crosslinked P(MA-PEG-BP), the diameter of these particles increased from 1.37±0.07 to 1.57±0.05 µm, so that the coating thickness of the crosslinked P((MA-PEG-BP) is 0.2±0.02 µm.

The crosslinked P(MA-PEG-BP)/PS core-shell micrometer-sized particles, on the other hand, possess bumpy surfaces, as illustrated in FIG. 12B. This bumpy morphology is probably due to the coating of the crosslinked P(MA-PEG-BP) nanoparticles onto the smooth surface of the PS microspheres.

Figure 13:
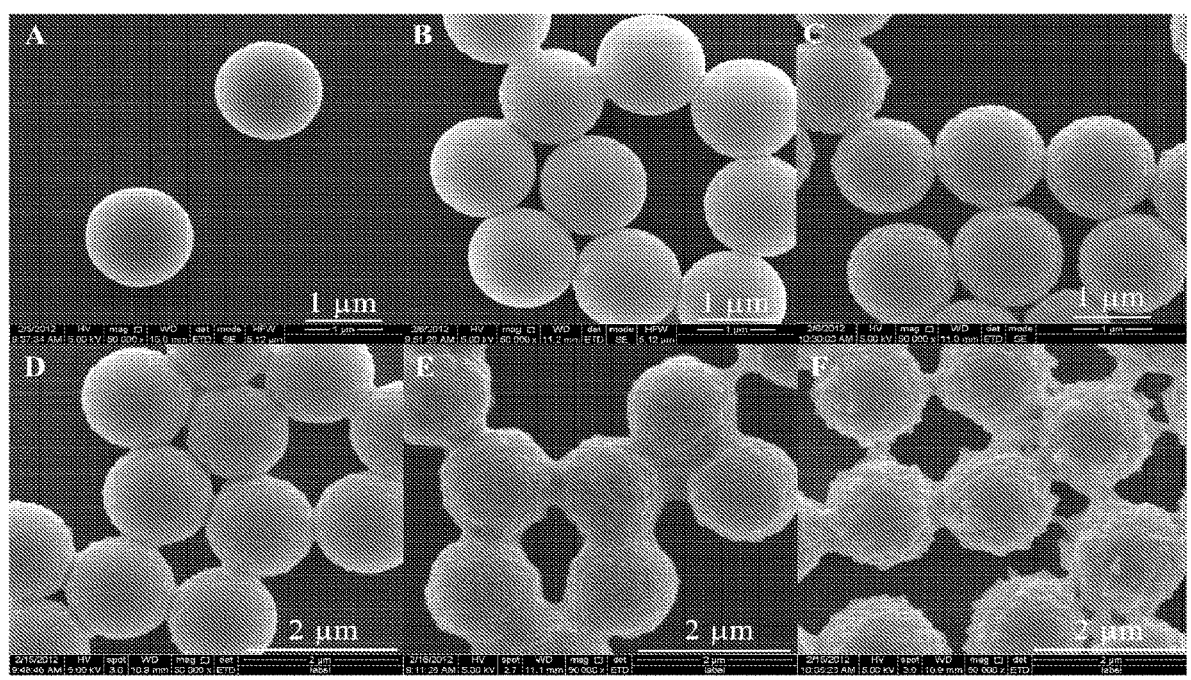
FIG. 13. Depicts SEM photomicrographs of the core PS particles (A) and the core-shell particles formed by dispersion polymerization of MA-PEG-BP and EDMA at different volume ratios of [EDMA]/[MA-PEG-BP]: 0.01 (B), 0.05 (C) 0.1 (D), 0.3 (E) and 0.5 (F), according to the description in example 9.

FIG. 13 shows SEM photomicrographs of the P((PEG-BP)/PS core-shell particles, produced by seeded dispersion copolymerization of MA-PEG-BP and the crosslinker monomer EDMA in the presence of the PS core microspheres, with increasing volume ratio of [EDMA]/[MA-PEG-BP] (0.01, 0.05, 0.1, 0.3 and 0.5), while maintaining the total volume of the monomers to be 100 mg. FIG. 13 also demonstrates the change in the morphology of the crosslinked P(MA-PEG-BP)/PS core-shell microparticles as function of the change in the volume ratio [EDMA]/[MA-PEG-BP], e.g., increasing this ratio resulted in more distorted morphology and roughen surfaces. The distorted morphology is probably attributed to the presence of the crosslinker monomer (EDMA) which enables the copolymers to grow only in specific directions.

Similar results were obtained when the PPS and the PS particles were replaced with PS microspheres grafted with hydroperoxides. These core-shell particles can be prepared in sizes ranging between approximately 40 nm to few microns depending on the diameter of the PS core particles and the polymerization conditions. The PS core particles of this invention may also be replaced by other core particles such as polydivinyl benzene and PMMA nano/micro particles.

Example 10: Synthesis of Crosslinked P(MA-PEG-BP) Hollow Particles

Crosslinked hollow P(MA-PEG-BP) particles were prepared by dissolution of the PS core part of the crosslinked P(MA-PEG-BP)/PS core-shell microspheres prepared as described in the previous example. In a typical experiment, 50 mg of the dried P(MA-PEG-BP)/PS core-shell microspheres were dispersed in 20 ml of dry acetone. The mixture was then shaken at room temperature for a 30 min. The obtained soluble PS acetone solution was then removed from the remaining hollow crosslinked P(MA-PEG-BP) microspheres by centrifugation. The obtained microspheres were then redispersed in dry acetone, and the former procedure was repeated. This process, related to the extraction of the soluble PS from the crosslinked P(MA-PEG-BP) hollow microspheres, was repeated several times, until the extracted acetone solution was free of residual PS. This was confirmed by obtaining a transparent solution after transferring 1 ml of the acetone solution to 5 ml of water. The remaining crosslinked hollow P(MA-PEG-BP) particles were then dried by lyophilization.

Figure 14:
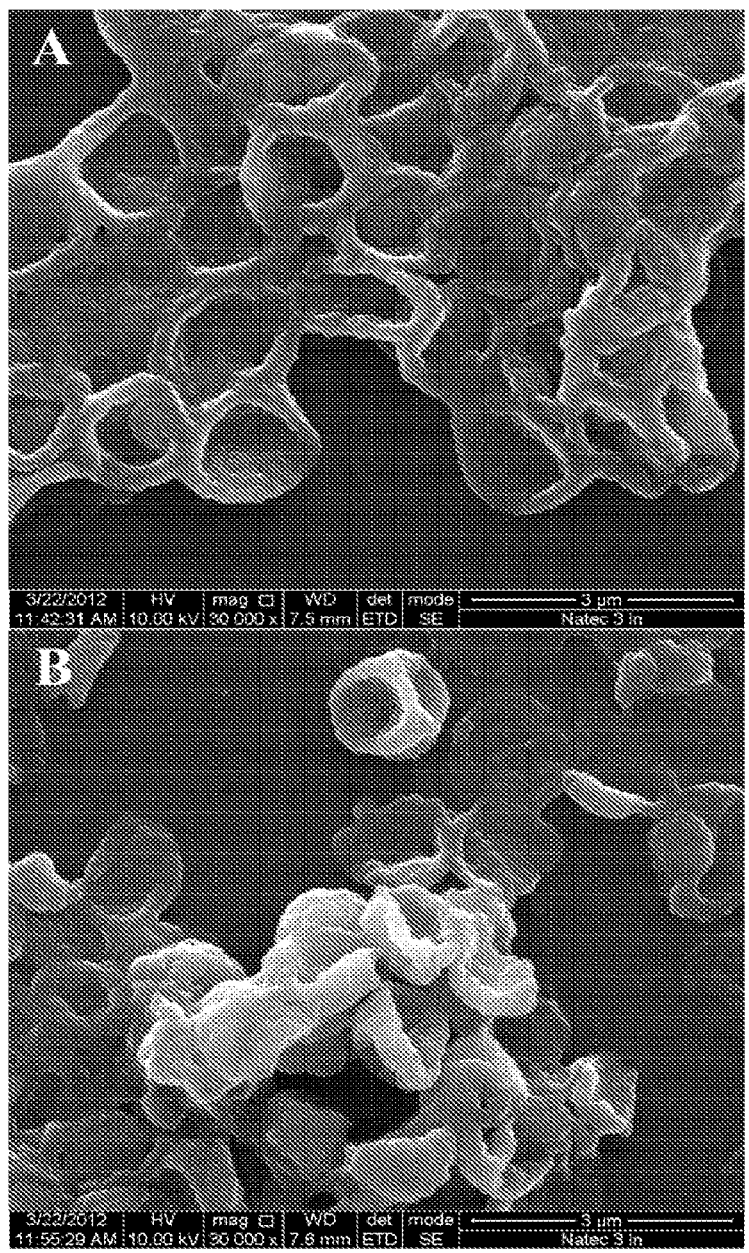
FIG. 14. Depicts SEM photomicrographs of the cross-linked P(MA-PEG-BP) hollow particles formed by dissolution of the PS part of the crosslinked P(MA-PEG-BP/PS/ microspheres prepared at mass ratio of [EDMA]/[MA-PEG-BP] of 0.5 (A) and 0.3 (B).

SEM photomicrographs of the obtained crosslinked hollow particles are shown in FIG. 14. It is interesting to realize that the structure and morphology of the formed materials are dependent on the mass ratio of [EDMA]/[MA-PEG-BP] as shown in FIGS. 14 A &B. The dissolution of the PS part of the P(MA-PEG-PB)/PS particles therefore resulted in a void formation belonging to the extracted PS. These voids can be distinguished from the remaining homogeneous particles, as observed by the SEM picture. These kind of hollow particles of controlled voids may be excellent scaffolds for tissue engineering. FIG. 14B illustrates that in the presence of relatively lower mass ratio of [EDMA]/[MA-PEG-BP], e.g., 0.3, after the dissolution of the PS part of the crosslinked P(MA-PEG-BP)/PS particles, folded, creased, and flattened particles were observed. This can be explained by the thinner P(MA-PEG-PB) shell obtained in the presence of 0.3 mass ratio of [EDMA]/[MA-PEG-BP] relative to 0.5 mass ratio.

Example 11: Preparation of Crosslinked P(MA-AL) and P(MA-PEG-AL) Nano/Micro-particles The following 2 sections disclose the formation of crosslinked P(MAL) and P(MA-PEG-AL) nano/micro-particles according to an embodiment of the invention.

(1) A mixture of MAL monomer (900 mg, 2.85 mmol), potassium persulfate (54 mg, 0.26 mmol), PVP (40 k, 60 mg) and EDMA (120 mg) in dist. water (9 ml) was shaken at 70° C. for 4 h. The resulting particles were washed and then analyzed for size and size distribution. Several monomer ratios were tested. The smallest nanoparticles (diameter <150 nm) were achieved for a ratio of [EDMA]/[MAL]=60/240 (w/w). Particles of sizes ranging from about 40 nm up to a few microns were formed by changing various polymerization parameters, e.g., monomer concentration, crosslinker monomer to MAL weight ratio, crosslinker monomer type and concentration, stabilizer/surfactant type and concentration, polymerization time, polymerization temperature, etc.

Crosslinked P(MA-PEG-AL) nanoparticles were prepared similarly substituting the MAL monomer for the MA-PEG-AL monomer. Water soluble P(MA-AL) and P(MA-PEG-AL) polymers were prepared similarly in the absence of the crosslinker monomer and the stabilizer and the presence of appropriate MA-AL and/or MA-PEG-AL concentration.

(2) A mixture of MA-AL monomer (600 mg, 1.9 mmol), glycidyl methacrylate (GMA) monomer (300 mg, 2.1 mmol), potassium persulfate (72 mg, 0.26 mmol), PVP (40 k, 60 mg) and EDMA (120 mg) in dist. water (12 ml) was shaken at 70° C. for 4 h. Particles of sizes ranging from about 40 nm up to a few microns were formed by changing various polymerization parameters, e.g., monomers concentration, co-monomer to MA-AL weight ratio, co-monomer type and concentration, stabilizer/surfactant type and concentration, polymerization time, polymerization temperature, etc.

Example 12: Preparation of Crosslinked P(St-BP) Particles

P(St-BP) microparticles of 475±71.42 nm diameter were formed by dispersion polymerization of the St-BP monomer. Briefly, microspheres of 475.83±71.42 nm were formed by the dissolution of 294 mg (3% w/v) St-BP, 100 mg PVP (1% w/v) and 30 mg PPS (10% w/w of the monomer) in 9.625 ml water, follow by adding 375 μl of concentrated HCl and 6.0 μl of EDMA. The 20 ml vial containing this solution was then shaken at 73° C. for 15 min. The polymerization process stopped by taking the vial out to an ice bath. The formed P(St-BP) microspheres were cleaned by dialysis.

Example 13: Preparation of Crosslinked P(St-BP)/PS Core-Shell Micrometer-sized Particles Oxidized PS microspheres of 2.18±0.23 μm were prepared as follow: 100 mg of PS microspheres of 2.1±0.17 μm were dispersed in 25 ml pure water, and then introduced into 250 ml round bottom flask. An O2/O3 stream containing an ozone output of 4 g/h was bubbled at room temperature through the dispersed microspheres for 2 min at a flow of 1 lit/min. The oxidized microspheres were then washed free of excess ozone by extensive centrifugation cycles with water.

P(St-BP)/PS microspheres of 2.52±0.35 μm were prepared by adding 100 mg of the St-BP monomer in 2 ml water to 3 ml of an aqueous dispersion of the oxidized PS microspheres (100 mg) of 2.18±0.23 μm. The total volume of water is therefore 5 ml and the St-BP concentration is 2% w/v. For the polymerization of St-BP, the vial containing the above mixture was purged with nitrogen to exclude air and then was shaken at 73° C. for 18 h. The resulting core-shell micrometer-sized particles were washed off excess reagents, including non-grafted St-BP by several centrifugation cycles with water, the washed core-shell particles were then dried by lyophilization.

These core-shell particles can be prepared in sizes ranging between approximately 40 nm to few microns depending on the diameter of the PS core particles and the polymerization conditions. The PS core particles of this invention may also be replaced by other core particles such as polydivinyl benzene and PMMA nano/micro particles.

Example 14: Preparation of BPs Core-shell Magnetic Nanoparticles

Iron oxide nanoparticles of sizes ranging from approximately 5-100 nm were prepared according to the literature (Molday and Mackenzie, J. Immunol. Methods, 1982, 52(3) 353-367; Margel S., Gura, S. Nucleation and growth of magnetic metal oxide nanoparticles of controlled size distribution and its use. EC 1088315 (2003); Israel 139638 (2006)). The BPs vinylic monomers were then polymerized in aqueous continuous phase in the presence of the core iron oxide nanoparticles as mentioned in examples 9 and 13. The purification of the BPs core-shell magnetic nanoparticles from undesired compounds was performed via magnetic columns. Commonly the weight % concentration of the dispersed iron oxide nanoparticles in the aqueous continuous phase was between 1-2 mg/ml. The total monomer/s concentration was between 0.5-2% of the aqueous solution, and the initiator concentration was between 1-5% of the total monomer/s. The polymerization temperature was 60-80° C., or RT if redox initiators were used.

Example 15: Inhibition of HAP Dissolution

BPs possess very strong affinity to HAP (hydroxyapatite), the inorganic bone mineral. As a result, HAP affinity tests are the most common in vitro tests for bone-seeking properties of new compounds. The current, novel, BP-containing monomers and nanoparticles were assayed for inhibition of HAP dissolution, in comparison to alendronate.

The test based on a slightly modified method of Francis et al. (Francis, M. D. The inhibition of calcium hydroxyapatite crystal growth by polyphosphonates and polyphosphates. Calcif Tissue Res 1969, 3, 151-162). The extent of HAP formation in the presence of inhibitors was studied in supersaturated calcium phosphate solutions.

The final concentration of calcium ($CaCl_2.2H_2O$) and phosphate ($K_2HPO_4$) ions in the incubation solutions was 3.87 mM and 2.32 mM, respectively, yielding a molar ratio of $[Ca]/[PO_4]=1.67$, as in hydroxyapatite (HAP). Each salt solution was prepared in 0.05 M Tris buffer, pH 7.4. The tested BP compound (1 mM) was dissolved in 4.64 mM $K_2HPO_4$ (5 ml). 5 ml of 7.74 mM $CaCl_2.2H_2O$ solution containing the BP compound and 5 ml of the 4.64 mM $K_2HPO_4$ were mixed in borosilicate glass vials (acid and acetone washed). The vials were then placed in a shaker at 37° C. for 24 h. The vials contents were centrifuged (4 min, 4000 rpm) and the supernatants were then separated and analyzed for calcium concentration by ICP Analysis. Table 1 shows several typical inhibition results.

TABLE 1

Inhibition % of Ca ion dissolution by various BPs compounds and particles

| Compound Type | Calcium ions concentration in filtrate (% of initial concentration) |
|---|---|
| Alendronate (1 mM) | 35 |
| St-BP monomer (1 mM) | 45 |
| MA-PEG-BP monomer (1 mM) | 43 |
| MA-BP(1 mM) | 40 |
| Crosslinked P(MA-PEG-BP) (3 mg) | 38 |
| Crosslinked P(MAL) (3 mg) | 41 |
| Crosslinked P(MA-BP) (3 mg) | 40 |

Example 16: Synthesis of Aqueous Soluble BPs Polymers

Aqueous soluble BPs polymers were prepared as described in examples 1-12 in the absence of the crosslinker monomer, by homopolymerization of the BP monomer or copolymerization of the BP monomer with a second monomer, e.g., APMA (N-(3-Aminopropyl)methacrylamide hydrochloride and/or acrylic acid, thus obtaining water soluble BP polymers. The Mw of these BP water soluble polymers could be controlled by changing polymerization parameters such as total monomer concentration and initiator concentration.

Example 17: Fluorescent Particles-Binding of Cy7-NHS Ester to BPs Nanoparticles

In a typical experiment, BP nanoparticles of 27±5 nm dry diameter were prepared by a dispersion co-polymerization process in BB (0.1 M, pH 8.4) as continuous phase, according to FIG. 1. 32,33 For this purpose, 45 mg MA-PEG-BP, 5 mg APMA and 50 mg TTEGDA (total monomers concentration was 5% w/v) were added to a vial containing 8 mg of PPS (8% w/w) as initiator and 20 mg PVP 360K (1% w/v) as stabilizer dissolved in 2 mL of BB. For the polymerization, the vial containing the mixture was purged with nitrogen gas to exclude air and then shaken at 83° C. for 8 h. The obtained particles were washed of excess reagents by extensive dialysis cycles (cut-off of 1000 k) with double distilled (DD) water. The effect of various polymerization parameters such as total monomers concentration, initiator type and concentration and stabilizer m.w. and concentration on the particles size, size distribution and polymerization yield was also studied.

The polymerization yield of the crosslinked BP nanoparticles was calculated by the following expression: Polymerization yield=(W particles)/W total monomers)×100, Where W particles is the weight of the dried particles and W total monomers is the initial weight of the polymerized monomers.

BPs nano/micro particles (e.g., P(MA-PEG-BP) particles from example 7) were reacted with Cy7-NHS ester in a weight ratio of 1:10. 1 mg of Cy7-NHS ester was dissolve in 1 ml of anhydrous DMSO. 500 µL of the Cy7-NHS ester in the anhydrous DMSO were added to 5 ml of the BPs nano/micro particles aqueous dispersion (1 mg/ml), and the reaction was stirred overnight. By adding 1 mg of PEG-NHS in a weight ratio of 1:5 to the aqueous dispersion, blocking of primary amines was accomplished. The reaction was done overnight at RT.

Absorption and Fluorescence Spectra of the BPs Nano/Micro Particles

Figure 15:
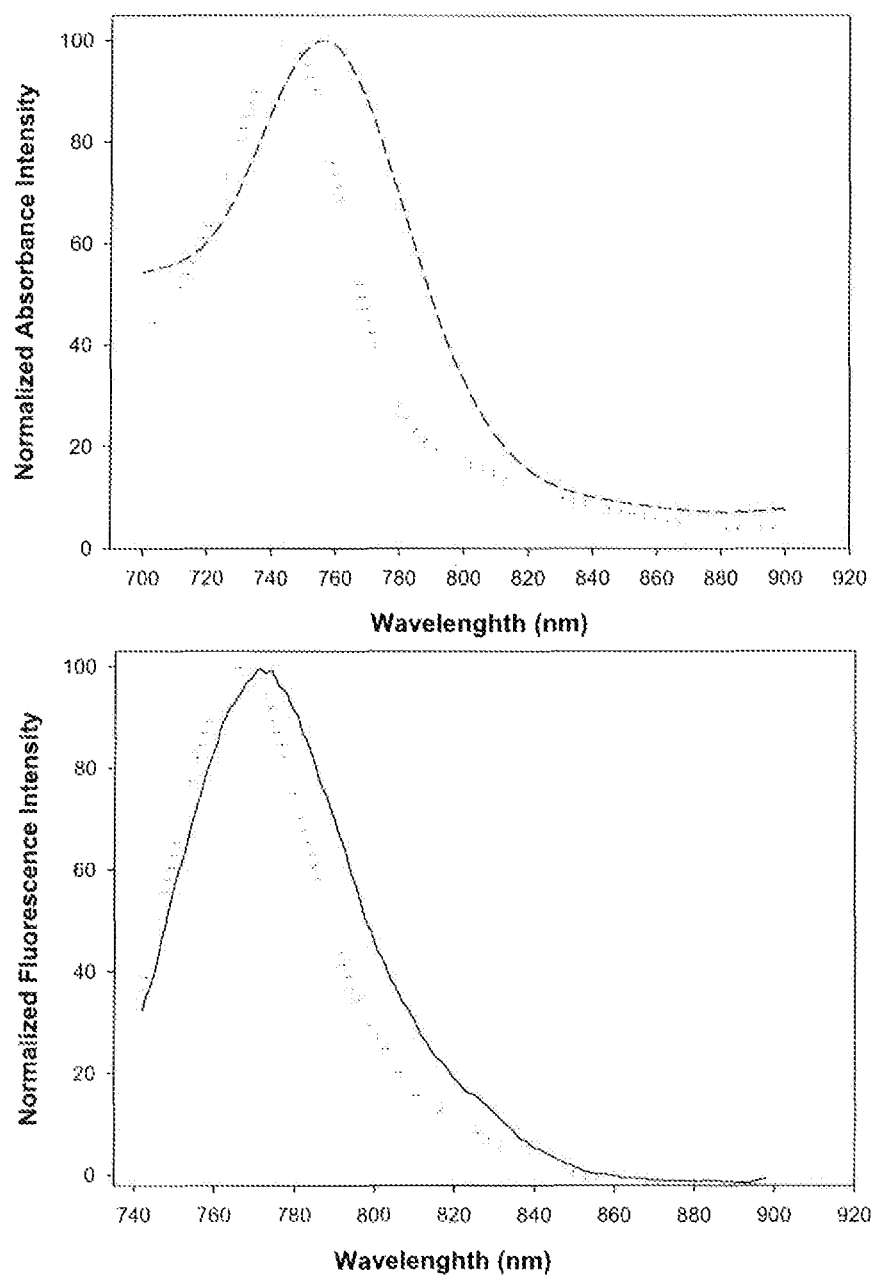
FIG. 15. Are graphs showing normalized absorbance (A) and emission (B) spectra of free Cy7 dye (dotted line) and Cy7 attached to the BPs nanoparticles (solid lines)

FIG. 15 exhibits the absorption (A) and fluorescence emission (B) spectra of free Cy7 dye and the Cy7 attached to the nanoparticles. The maximum absorption of free Cy7 and NIR fluorescent dye nanoparticles occurs at approximately 745 and 755 nm, respectively. The maximum fluorescence emission intensity occurs at approximately 765 and 775 nm, respectively. The red-shift of the NIR fluorescent nanoparticles compared to free Cy7 dye is probably due to covalent binding of the dye to the nanoparticles that affects the dipole moment of the dye.

Figure 16:
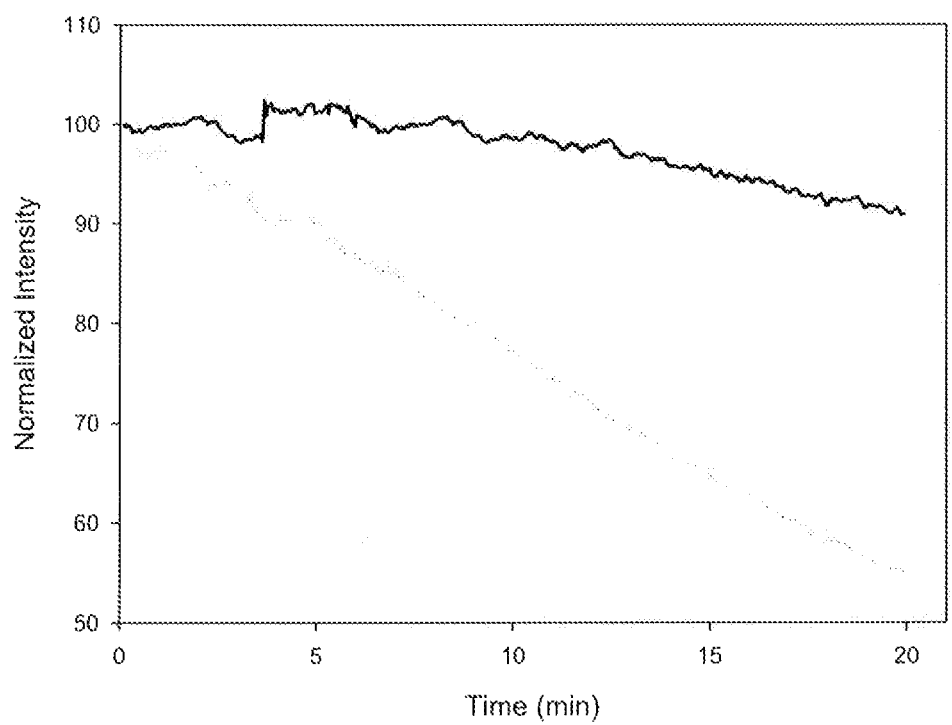
FIG. 16. Is a graph showing the photostability of the Cy7-BPs nanoparticles (A) and free Cy7 (B) as a function of time. Samples of Cy7 attached to the nanoparticles and free Cy7 were illuminated with a Xenon flash lamp for 20 min as described in the experimental part.

Photobleaching experiments were performed for the free Cy7 dye and the Cy7 attached to the BPs nanoparticles, in order to examine their photostability. Samples of the free Cy7 dye and the Cy7 attached to the nanoparticles were illuminated at 740 nm and their fluorescence intensities were measured. It was demonstrated that, during illumination, the fluorescence intensity of the Cy7 attached to nanoparticles remained almost unaltered while that of the free Cy7 decreased significantly, as shown in FIG. 16.

Photobleaching is the irreversible light-induced destruction of the fluorophore, affected by factors such as oxygen, oxidizing or reducing agents, temperature, exposure time and illumination levels. FIG. 16 demonstrates that the attachment of the dye to the nanoparticles reduced photobleaching. The covalent attachment of the dye probably protects the dye against reactive oxygen species thereby reducing the Photobleaching.

Example 18: IV Injection to Chicken Embryos of the Bone-targeted Near-infrared Fluorescent P(MA-PEG-BP) Nano/Micro Particles Near infrared fluorescence (NIR) nano/micro BPs particles were prepared by dispersion polymerization, according to example 7. Cy-7 NHS ester was attached to the BPs particles according to example 17. Then the fluorescent BPs nano/micro particles were IV injected to a chicken embryo model for biodistribution and bone uptake study.

Fertile chicken eggs obtained from a commercial supplier were incubated at 37° C. at 60-70% humidity in a forced-draft incubator. On embryonic day E14 of incubation, a window was opened in the shell and the chorioallantoic membrane (CAM) was exposed. A total of 100 µl of the fluorescent nanoparticles dispersed in PBS with 3 different concentrations (0.25, 0.5 and 1.0 mg/ml) and PBS buffer as a control were injected intravenously into a large CAM blood vessel. Then, the window in the egg's shell was sealed with sellotape and chicken embryos were returned to incubation for different time's periods (1, 4, 6, 24, 48 and 96 h). Each experiment at a specific concentration and time interval contained 4 chicken embryos.

Whole body distribution of the Cy7-BP BPs nanoparticles was studied by Maestro in-vivo fluorescence imaging system. The system is equipped with a fiber-delivered 300 W xenon excitation lamp, and images can be acquired from =500-950 nm by 1.3 megapixel CCD camera. Image cubes of the whole body, blood and the removed organs, e.g., bones, liver, kidney, heart and spleen, were taken. The organs were washed extensively in PBS. The organ samples were transferred onto black paper, and blood samples were transferred onto black 96 wells plate before imaging. 10 µl of heparin was added to each 90 µl of blood samples to avoid coagulation. Fluorescence intensity measurements were performed using ImageJ NIH (National Institutes of Health) software.

Figure 17:
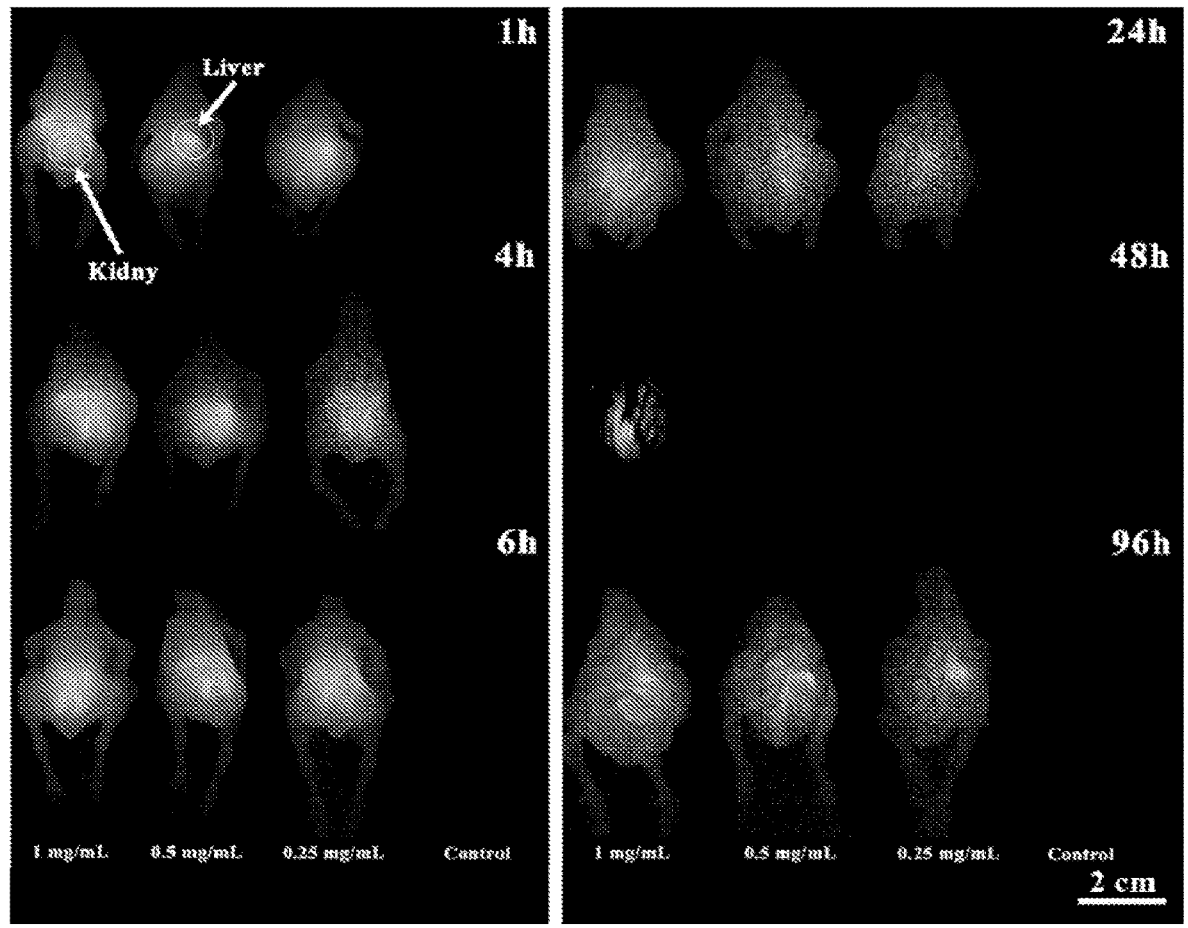
FIG. 17. Is a micrograph showing the fluorescence intensity of the imaged chicken embryos in the first hour (A), 4 h (B) 6 h (C), 24 h (D), 48 h (E), and 96 h (F), at various concentrations.

FIG. 17 illustrates increasing fluorescence intensity of the imaged chicken embryos in the first six h at all concentrations. 24 h after the injection a decrease in the fluorescence intensity was observed. At 48 h most of the fluorescence intensity was lost, possibly due to the fact that the BPs nanoparticles are extracted from the body to the allantois system (part of a developing animal conceptus, assisting the embryo to exchange gases and handles liquid waste). 96 h after the injection the imaged chicken embryos surprisingly increased, probably due to the escape of the BPs fluorescent nanoparticles from the allantois system back to the body. Most of the fluorescence observed at FIG. 17 can be ascribed to the liver and kidney area as indicated by the arrows in FIG. 17.

Bones

BPs are known for their strong chelation to calcium ions which is observed in bone and bone mineral [hydroxyapatite, (HAP)]. In this study novel BPs nanoparticles were synthesized. These types of nanoparticles should increase the half-life time of these nanoparticles in the blood, and utilize the BPs nanoparticles as targeting moieties for specific bone imaging and therapy.

Figure 18:
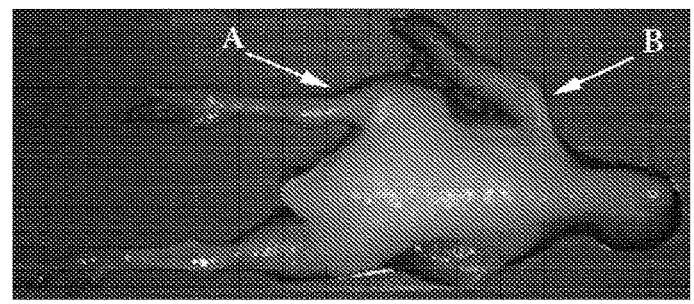
FIG. 18. Is a Black and white photograph of the chicken embryo before the removal of tibiotarsus (A) and humerus (B) bones.

Tibiotarsus (A) and humerus (B) bones (FIG. 18) were taken from the chicken embryo in each injection interval time, then washed extensively with PBS and fluorescence images were acquired, in order to examine the biodistribution of the BPs nanoparticles in the chicken embryo bones.

Figure 19:
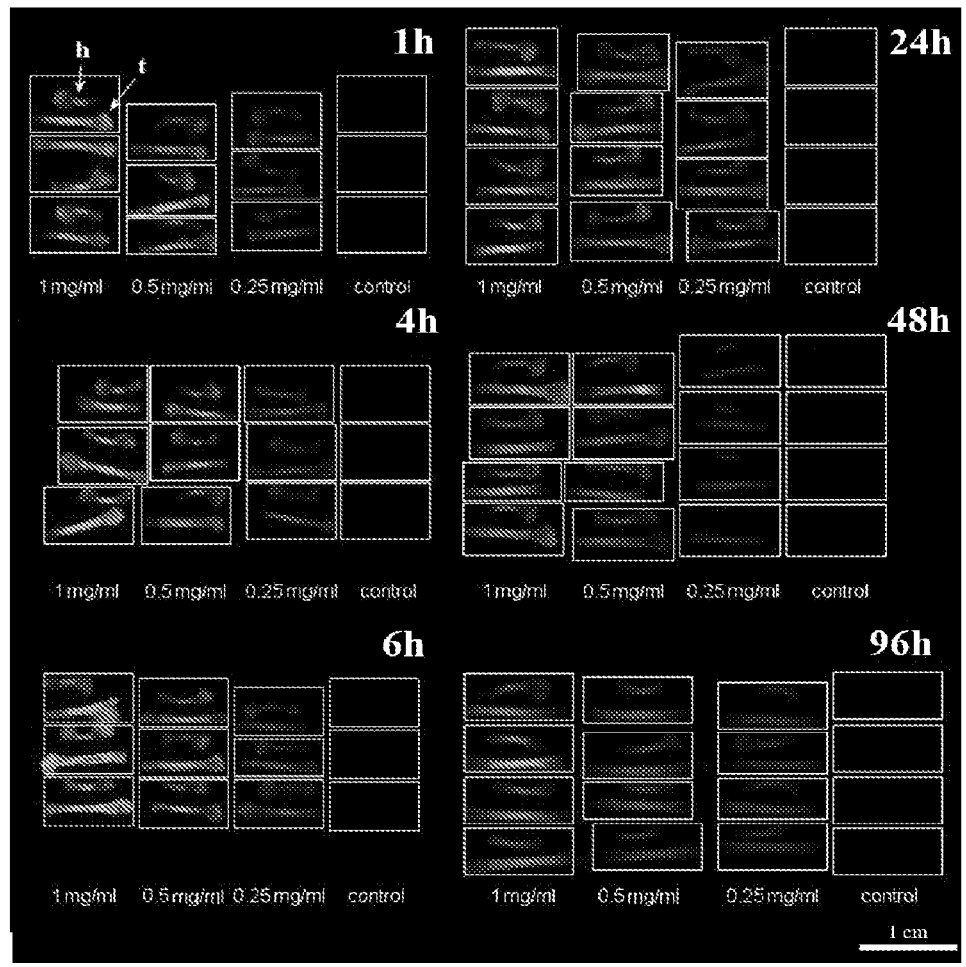
FIG. 19. Is a micrograph showing the effect of the concentration of BPs nanoparticles on their content in the tibiotarsus (t) and humerus (h) bones after 1, 4, 6, 24, 48 and 96 hours (h). Each rectangle represents a different embryo. This experiment was performed with 3 chicken embryos at 1, 4 and 6 h, and four chicken embryo at 24, 48 and 96 h as described in the experimental part. The fluorescence intensity of the BPs nanoparticles in the bones, unlike in other organs (see FIG. 20), does not decrease significantly during the experiment. All three concentrations showing fluorescence while the control (PBS) shows no fluorescence.

Bones fluorescence image (FIG. 19) showed the BPs nanoparticles content in the bones after 1, 4, 6, 24, 48 and 96 h. All three concentrations showed high fluorescence intensity and as the concentration decreased the fluorescence intensity decreased. The control (PBS) did not indicate detectable fluorescence.

By comparing bones to other organs (FIG. 20) it was seen that the fluorescence decrease in the bones during time is significantly lower than that observed for the other organs (FIG. 20) and the whole body (FIG. 17), this is probably due to the strong chelation of the BPs nanoparticles to the bone.

Organs Biodistribution

Liver, kidney, heart and spleen were taken from the chicken embryo in each interval of time, washed extensively with PBS and fluorescence images were then acquired. The organ samples were transferred onto black paper. In addition, 90 µl of blood was taken from chorioallantoic membrane blood vessel in each interval of time and was distributed in a 96 black well plate with additional 10 µl of heparin to avoid coagulation.

Figure 20:
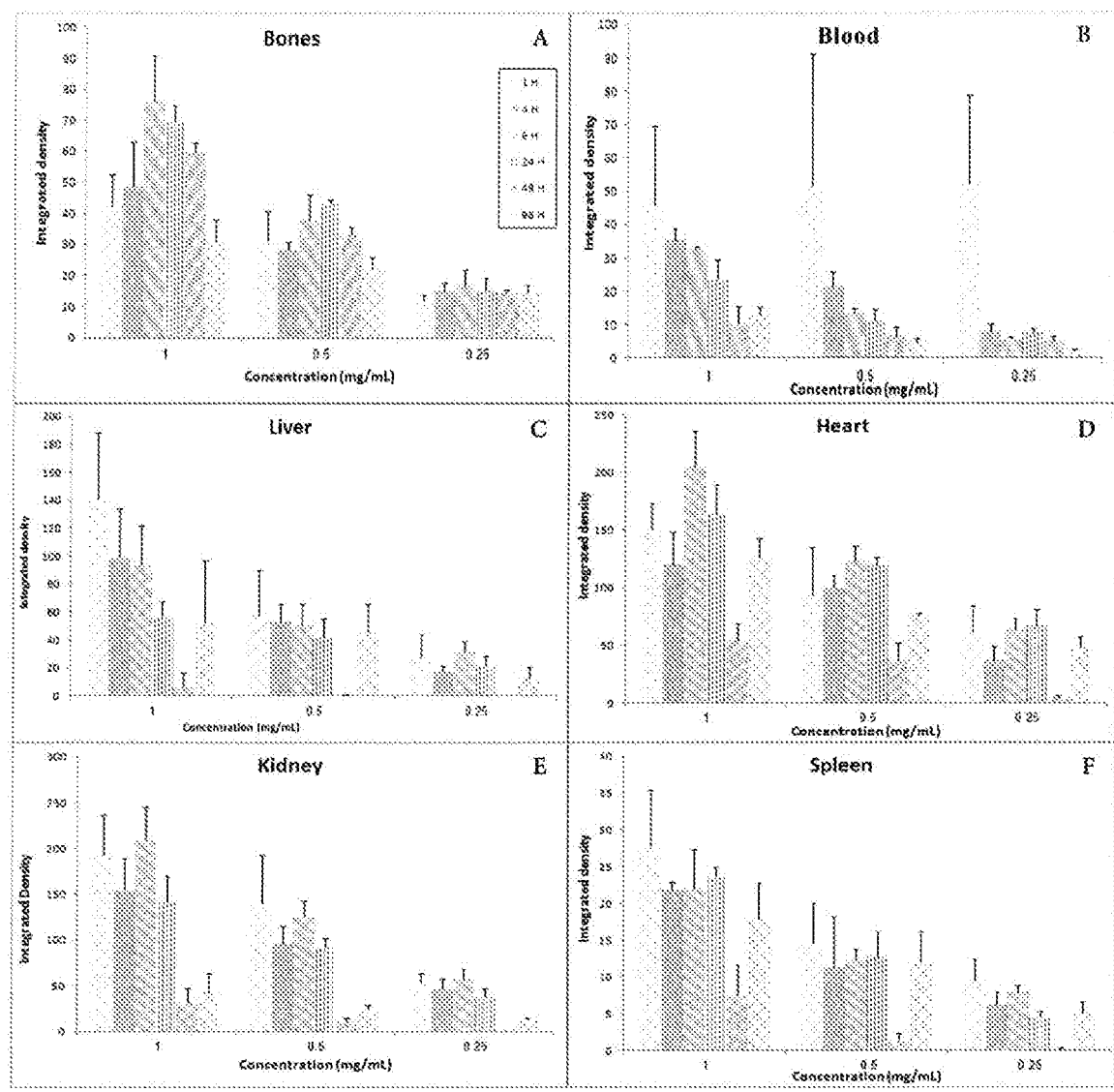
FIG. 20. Are bar graphs showing the fluorescence intensity measured by image-J software of Bones (A), Blood (B), Liver (C), Heart (D), Kidney (E) and Spleen (F).
Figure 21:
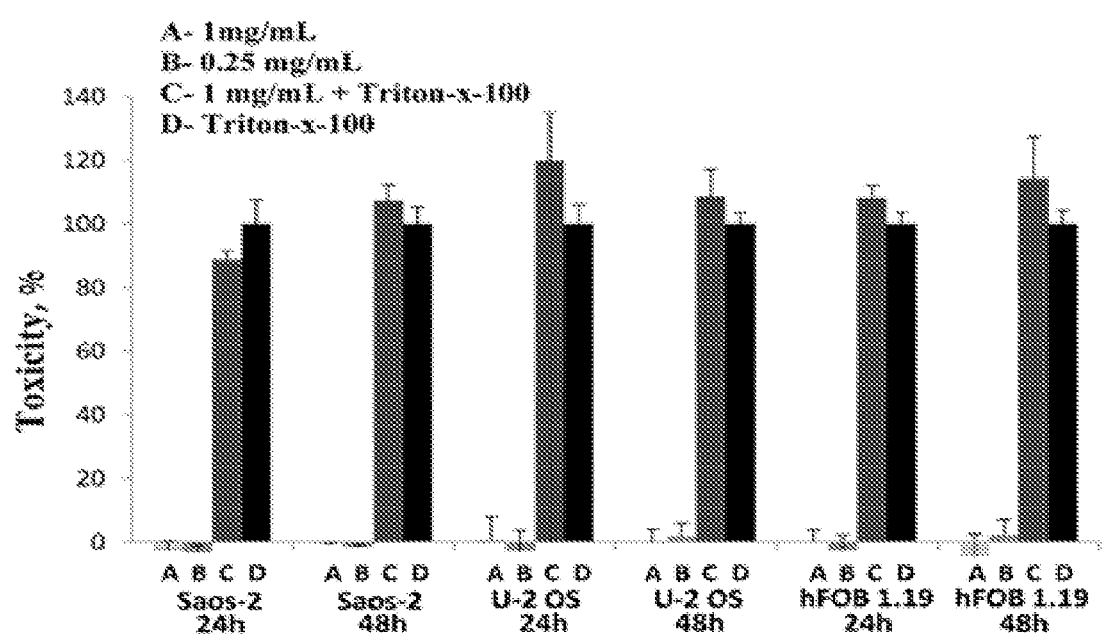
FIG. 21. Is a bar graph showing the cytotoxic effect of the BP nanoparticles on human osteosarcoma (Saos-2 and U-2 OS) and hFOB 1.19 human osteoblast cells measured by the LDH assay. Cells ($3\times10^5$) were incubated for 24 and 48 h with the BP nanoparticles (0.25 and 1 mg/mL). Cells were incubated with Triton x-100 1% as positive control (100% toxicity). Non-treated cells (negative control) were similarly incubated. Each bar represents mean±standard deviations of 4 separate samples.

BPs nanoparticles uptake could be observed from fluorescence intensity shown in the blood, liver, kidney, heart and spleen in the same manner as in the bones. A similar behavior of the organs to that of the whole body was observed, i.e., increase in the fluorescence intensity of the organs after 1, 4, and 6 h, followed by decrease after 24 and 48 h and again increase after 96 h. As it was explained earlier for the whole body results the increase in the fluorescence after 96 h is probably due to the return of the BP nanoparticles from the allantois system to the different organs. Contrarily to the whole body and the organs behavior, a continuous decrease in the fluorescence intensity was observed in the blood (FIG. 20).

Example 19: LDH In-vitro Cytotoxicity Test of the BPs Nano/Micro Particles

In vitro cytotoxicity of the BPs particles (example 7) was tested by using three cancer cell lines: human osteosarcoma Saos-2, U-2 OS and mouse macrophage Raw 264.7. All cell lines are adherent to the used culture dishes. All cultures were grown in DMEM that was supplemented with 10% heat-inactivated fetal bovine serum (FBS), 1% glutamine and 1% penicillin/streptomycin. Cell lines were screened to ensure they remained mycoplasma-free using Mycoplasma Detection Kit. The cell cytotoxicity was assessed by measuring the release of cytoplasmic lactate dehydrogenase (LDH) into cell culture supernatants. LDH activity was assayed using the Cytotoxicity Detection Kit according to the manufacturer's instructions (Decker, T. and M. L. Lohmannmatthes, A Quick and Simple Method for the Quantitation of Lactate-Dehydrogenase Release in Measurements of Cellular Cyto-Toxicity and Tumor Necrosis Factor (Tnf) Activity. Journal of Immunological Methods, 1988. 115(1): p. 61-69.).

Cells were seeded ($3 \times 10^5$ cells per well) and grown to 90-95% confluency in 24 well plates before treatment with the BPs nanoparticles. Cell cultures that were not exposed to the BPs nanoparticles were included in all assays as negative controls. Cell cultures that were treated with 1% triton-x-100 used as positive controls. To test if the BPs nanoparticles can interact with LDH kit compounds, cell cultures exposed to a mixture containing maximal BPs nanoparticles concentration dispersed in PBS and 1% Triton-x-100.

The BPs nanoparticles were freshly dispersed in PBS and then added to the 95% confluent cell culture in culture medium containing 0.25 and 0.5 mg/ml. The cell cultures were further incubated at 37° C. in a humidified 5% CO2 incubator and then checked for cellular cytotoxicity at intervals of 24 and 48 h. The percentage of cell cytotoxicity was calculated using the following formula as shown in the manufacturer's protocol. All samples were tested in tetraplicates.

When tested by the LDH quantitative assay, nanoparticles concentrations of 0.25 and 0.5 mg/ml had no cytotoxic effect on the human osteosarcoma cell lines: Saos-2 and U-2 OS (FIG. 22). Treatment of Raw 264.7 mouse macrophage cells with maximal BP nanoparticles concentration (0.5 mg/ml) produced minor LDH levels (11.7%) after 48 h when compared to untreated (blank) cells, indicating minor or insignificant toxicity to these macrophage cell line.

Example 20: Synthesis of Small BPs Molecules-Synthesis of BPs PEG Derivatives $NH_2$-PEG-COOH m.w=2000 (150 mg, 0.5 mmol) was dissolved in dry dichloromethane (5 ml). DMF (1 drop) was added as catalyst, followed by oxalyl chloride (127 μL, 1 mmol, 2 eq.). Gas evolution was observed, the mixture was stirred at rt overnight and gradually turned orange. The resulting mixture was evaporated to dryness, yielding an orange oil which was dissolved in THF (5 ml). Tris(trimethylsilyl)phosphite (0.298 ml, 1 mmol, 2 eq.) was added and the mixture was stirred at rt for 1 h. The mixture was evaporated to dryness, methanol (5 ml) was added and the dark mixture was stirred overnight at rt. The mixture was again evaporated producing the $NH_2$-PEG-BP molecule.

1H, 31P and 13C NMR showed desired product. The NH2-PEG-BP was further tested for bone uptake by conjugating Cy-7-NHS ester dye molecules to the primary amine. The dyed conjugate illustrated high bone specificity to chicken embryo and young mouse models.

Example 21: Synthesis of BPs Dyed Small Molecule

Cysteamine was bound to MA-PEG-BP monomer by Michael addition reaction in PBS (pH 7.4). Cy-7-NHS ester dye molecules were then bound to the cysteamine-conjugated MA-PEG-BP via its primary amine functionality. The dyed conjugate illustrated high specificity to bones of chicken embryo and young mouse models.

Example 22: Preparation of ICG-BP Conjugate

ICG-mono carboxylic acid was converted to ICG-BP according to example 20 substituting the NH2-PEG-CO2H for the carboxylated ICG.

What is claimed is:

1. A particle comprising a compound or a polymer comprising a formula selected from the group consisting of:

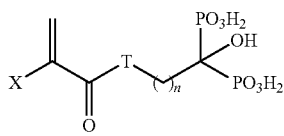
(i)

wherein X is H, $CH_3$, CN, phenyl, substituted phenyl, $(CH_2)_mZ$, or phenyl$(CH_2)_mZ$;
T is O, S or NH;
m equals 1 to 20;
n equals 1-100; and
Z is CN, $NH_2$, Thiol, OH, or $CO_2H$;

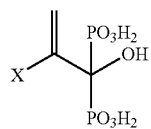
(ii)

wherein X is H, $CH_3$, CN, phenyl, substituted phenyl, $(CH_2)_mZ$, or phenyl$(CH_2)_mZ$; and
Z is CN, $NH_2$, Thiol, OH, or $CO_2H$;
or

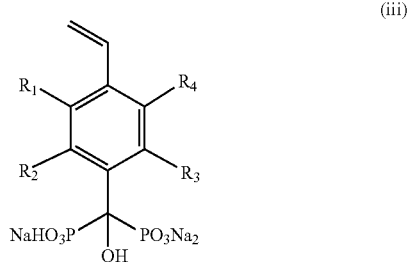
(iii)

wherein:
$R_1$, $R_2$, $R_3$, and $R_4$ are independently: H, $CH_3$, OH, or a halogen; and
wherein said particle has a particle size ranging from 40 nm to 2.2 μm.

2. The particle of claim 1, further comprising a biologically active molecule.

3. The particle of claim 1, wherein said compound or polymer is bound to a metallic core or a metallic oxide core via a reactive group.

4. The particle of claim 1, wherein said polymer is water soluble.

5. An article comprising a biocompatible or a plastic core coated with the particle of any one of claims 1 and 2-4.

6. A method of making the particle of claim 1, comprising the step of free radical homopolymerization or copolymerization of monomers of the compound of (i) to (iii), in the presence of:
    (a) a free radical homopolymerization or copolymerization initiator; and
    (b) a free radical homopolymerization or copolymerization stabilizer, thereby making the particle of claim 1.

7. The method of claim 6, wherein said making the particle is obtained in a reaction mixture, wherein said reaction mixture comprises:
    1-20% by weight of said monomers;
    0.2-50% by weight of said free radical homopolymerization or copolymerization initiator; and
    0.1-20% by weight of said free radical homopolymerization or copolymerization stabilizer.

8. A method of making the particle of claim 7, comprising a Michael addition reaction including:
    (a) thiolating a double bond within the compound or the polymer; and
    (b) binding the thiolated compound or polymer to an amino group within said biologically active molecule.

9. The method of claim 8, wherein said thiolating is obtained by 1,2-amino-thio-ethanol.

10. A method of imaging a bone in a subject, comprising the steps of:
    (a) administering to said subject a composition comprising an effective amount of the particle of claim 1 comprising a dye; and
    (b) irradiating said dye;
    thereby imaging a bone in a subject.

11. The method of claim 10, wherein said dye is covalently bound to said particle.

12. The method of claim 10, wherein said dye is physically entrapped within said particle.

13. A method of delivering a biologically active compound to a bone in a subject, comprising the step of administering to said subject a composition comprising an effective amount of the particle of claim 2, thereby delivering a biologically active compound to a bone in a subject.

14. A method of treating a bone related disease in a subject, comprising the step of administering to said subject a composition comprising an effective amount of the particle of claim 2, said particle of claim 2 comprises a bone related disease drug, thereby treating a bone related disease in a subject.

* * * * *